United States Patent
Fahrig et al.

(10) Patent No.: US 9,181,199 B2
(45) Date of Patent: Nov. 10, 2015

(54) URACIL DERIVATIVES AND USE THEREOF

(75) Inventors: Rudolf Fahrig, Dresden (DE); Kurt Eger, Tubingen (DE); Martin Fuhrer, Leipzig (DE); Nicole Heinze, Leipzig (DE); Matthias Klemm, Leipzig (DE); Jorg-Christian Heinrich, Dresden (DE)

(73) Assignee: RESprotect GmbH, Dresden (DE)

( * ) Notice: Subject to any disclaimer, the term of this patent is extended or adjusted under 35 U.S.C. 154(b) by 321 days.

(21) Appl. No.: 13/000,900

(22) PCT Filed: Jun. 25, 2009

(86) PCT No.: PCT/EP2009/004698
§ 371 (c)(1),
(2), (4) Date: Mar. 21, 2011

(87) PCT Pub. No.: WO2009/156182
PCT Pub. Date: Dec. 30, 2009

(65) Prior Publication Data
US 2011/0166096 A1    Jul. 7, 2011

(30) Foreign Application Priority Data
Jun. 25, 2008   (DE) .......................... 10 2008 030 091

(51) Int. Cl.
| | | |
|---|---|---|
| A61K 31/7072 | (2006.01) | |
| C07H 19/06 | (2006.01) | |
| C07D 239/54 | (2006.01) | |
| C07D 239/22 | (2006.01) | |

(52) U.S. Cl.
CPC ............ *C07D 239/54* (2013.01); *C07D 239/22* (2013.01)

(58) Field of Classification Search
CPC ............ A61K 31/7072; A61K 31/506; A61K 31/513; A61P 35/00; C07D 239/24; C07D 401/02; C07D 401/14; C07D 403/06; C07H 19/00
USPC .......... 514/50, 49, 51; 536/28.53, 28.54, 22.1
See application file for complete search history.

(56) References Cited

U.S. PATENT DOCUMENTS 5,859,014 A * 1/1999 Bantle et al. ............. 514/252.11
6,589,941 B1   7/2003 Fahrig et al.

FOREIGN PATENT DOCUMENTS

| DE | 202 873 | 10/1983 |
|---|---|---|
| DE | 696 12 698 T2 | 12/2001 |
| EP | 0 748 800 B1 | 5/2001 |
| WO | WO 96/23506 A1 | 8/1996 |
| WO | WO 01/07454 A1 | 2/2001 |
| WO | WO 02/083651 A2 | 10/2002 |
| WO | WO 2006/070292 A2 | 7/2006 |

OTHER PUBLICATIONS

Gauri et al. (Chemotherapy (Basel, Switzerland) (1969), 14(3), 159-70) (abstract sent).*
Allen et al. (Chemotherapy (Basel, Switzerland) (1985), 31(2), 151-9) (abstract sent).*
STN abstract of Trampota et al.; WO 2007059330; May 24, 2007) (abstract sent).*
Henriksen (Nucleosides, Nucleotides & Nucleic acids (2000), 19(7), 1093-1100).*
International Bureau of WIPO, International Preliminary Report on Patentability in International Application No. PCT/EP2009/004698 (Mar. 24, 2011).
Crisp et al., "Palladium-Catalyzed Coupling of a Propargylglycine Derivative," *Tetrahedron*, vol. 48. No. 15, pp. 3239-3250 (1992).
Desoize et al., "Multicellular resistance: a paradigm for clinical resistance?," *Critical Reviews in Oncology/Hematology*, Issue 36, pp. 193-207 (2000).
Fahrig et al., "Inhibition of Induced Chemoresistance by Cotreatment with (E)-5-(2-Bromovinyl)-2'-Deoxyuridine (RP101)," *Cancer Research*, vol. 63, pp. 5745-5753 (2003).
Fahrig et al., "RP101 improves the efficacy of chemotherapy in pancreas carcinoma cell lines and pancreatic cancer patients," *Anti-Cancer Drugs*, vol. 17, No. 9, pp. 1045-1056 (2006).
Hannon et al., "A new synthesis of N-blocked dihydrouracil and dihydroorotic acid derivatives using lithium tri-sec-butyl borohydride as reducing agent," *Tetrahedron Letters*, vol. 21, pp. 1105-1108 (1980).
Kundu et al., "Studies in uracil derivatives and analogs. 19. Synthesis of 5-(acylethynyl) uracils and their corresponding 2'-deoxyribonucleosides," *Journal of the Chemical Society, Perkins Translations 1: Organic and Bio-Organic Chemistry*, vol. 21, pp. 2657-2663 (1993). Abstract only.
Matsuhashi et al., "Synthesis of 5-substituted pyrimidine nucleosides through a palladium-catalyzed cross-coupling of alkylhalosilanes," *Heterocycles*, 42(1), pp. 375-384 (1996). Abstract only.
Mendiratta et al., "Structure-Activity Study on Antiviral 5-Vinylpyrimidine Nucleoside Analogs Using Weiner's Topological Index," *J. Chem. Inf. Comput. Sci.*, No. 34, pp. 867-871 (1994).

(Continued)

Primary Examiner — Shaojia Anna Jiang
Assistant Examiner — Michael C Henry
(74) Attorney, Agent, or Firm — Leydig, Voit & Mayer, Ltd.

(57) ABSTRACT

Disclosed are uracil derivatives of the formula (I):

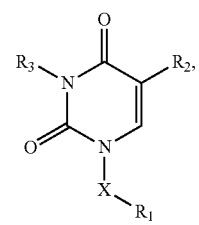

wherein $R_1$, $R_2$, $R_3$, and X are as defined herein, and use thereof as therapeutic agents. The uracil derivatives are used in particular together with a cytostatic agent for suppressing or reducing resistance building up on cytostatic treatment.

13 Claims, 13 Drawing Sheets

(56) References Cited

OTHER PUBLICATIONS

Takara et al., "An Update on Overcoming MDRI-Mediated Multidrug Resistance in Cancer Chemotherapy," *Current Pharmaceutical Designs*, No. 12, pp. 273-286 (2006).

International Search Report dated Jan. 4, 2010 for International Application No. PCT/EP2009/004698.
International Preliminary Report on Patentability for International Application No. PCT/EP2009/004698.

* cited by examiner

URACIL DERIVATIVES AND USE THEREOF

The invention concerns uracil derivatives and their use as therapeutic agents. Uracil derivatives are used, in particular together with a cytostatic agent, to suppress or reduce resistance formation during cytostatic treatment.

Chemotherapy is a standard treatment for cancers. Cytostatics affect cell division and accordingly are particularly toxic for rapidly growing tumor cells. Cytostatics induce apoptosis, i.e., they lead to cell death of the tumor cells. Unfortunately, the resistance-free period of treatment with the cytostatics that are currently on the market is for the most part not long enough to entirely eradicate the tumor. "Chemosensitizers" that counteract existing resistance were developed to improve this situation.

If the resistance is caused by amplification (multiplication) and over-expression of the "multi-drug resistance" gene (MDR-1), this can be reduced by inactivation of its gene product (P-glycoprotein) (Takara, K., Sakaeda, T., Okumura, K. 'An update on overcoming MDR1-mediated multidrug resistance in cancer chemotherapy.' Curr. Pharm. Des. 2006; 12(3):273-86).

Up to now, serious side effects have been standing in the way of using P-glycoprotein inhibitors. Third generation substances can probably be used only for a short-term treatment because of their toxic effect and also only in the case of the few tumors whose resistance stems exclusively from the effect of the "multi-drug resistance" gene. In addition, inhibitors of the receptors for tyrosine kinase or the over-expression of individual oncogenes were developed. However, still only a few suitable tumors can be treated (Desoize, B., Jardillier, J., 'Multicellular resistance: a paradigm for clinical resistance?' Crit. Rev Oncol Hematol. 2000; 36:193-207).

5-Substituted nucleosides for inhibition of resistance formation in cytostatic treatment are known from EP 0 806 956. The compounds listed there are (E)-5'-(2-bromovinyl)-2'-deoxyuridine (BVDU) and (E)-5'-(2-bromovinyl)uracil (BVU).

These agents prevent resistance formation and combat resistances that do not already exist. In contrast to the attempts to circumvent or reduce existing chemoresistances, which have been known for decades and for the most part have been unsuccessful, there is currently no competition anywhere in the world for this technological approach (Fahrig, R., Heinrich, J. C., Nickel, B., Wilfert, F., Leisser, C., Krupitza, G., Praha, C., Sonntag, D., Fiedler, B., Scherthan, H., and Ernst, H. 'Inhibition of induced chemoresistance by cotreatment with (E)-5-(2-bromovinyl)-2'-deoxyuridine (RP101).' Cancer Res. 63 (2003) 5745-5753). The first drug BVDU showed a statistically significant effect in two clinical studies with pancreatic cancer patients. The effect of cotreatment of cytostatics with BVDU was more effective than any of the other previously described chemotherapies (Fahrig, R., Quietzsch, D., Heinrich, J.-C., Heinemann, V., Boeck, S., Schmid, R. M., Praha, C., Liebert, A., Sonntag, D., Krupitza, G., and Haenel, M.; 'RP101 improves the efficacy of chemotherapy in pancreas carcinoma cell lines and pancreatic cancer patients.' Anti-Cancer Drugs 17, 1045-1056, 2006).

For this reason a task of this invention was to make available substances that have a higher efficacy with regard to suppression or reduction of resistance formation during cytostatic treatment than the other compounds known from the prior art.

This task is solved by the uracil derivatives disclosed herein, for example, the uracil derivatives are made available for use as therapeutic agents. The uracil derivatives can be used to suppress or reduce resistance formation during cytostatic treatment. Further advantages are also disclosed.

In accordance with the invention uracil derivatives of General Formula I are made available:

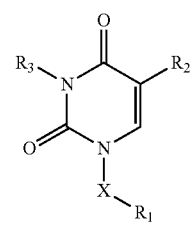

I where:

$R_1$ is chosen from the group consisting of linear or branched $C_2$-$C_{18}$ alkenyl, linear or branched $C_2$-$C_{18}$ alkynyl, unsubstituted or substituted aromatic residues having 6-22 carbon atoms, and/or unsubstituted or substituted heteroaromatic residues having 5-22 carbon atoms, $C_5$-$C_8$ cycloalkyl, $C_5$-$C_8$ cycloalkenyl, adamantyl;

X is a single bond or is chosen from the group consisting of $(CHR_4)_n$ with n=1-3, CO, $CNR_4$, CNOH, SO, and $SO_2$, where $R_4$ is chosen from the group consisting of H, linear or branched $C_1$-$C_{18}$ alkyl residues of the formulas II-IV,

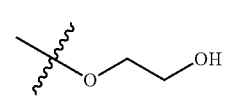

II

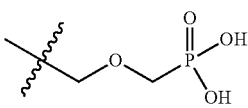

III

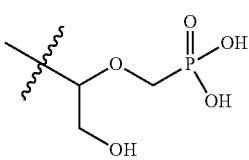

IV and residues as defined for $R_1$;

$R_2$ is chosen from the group consisting of a) saturated residues chosen from the group consisting of linear or branched $C_3$-$C_{18}$ alkyl or residues of General Formula V:

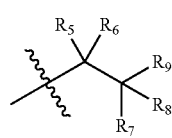

V where $R_5$-$R_9$ are each independently chosen from the group consisting of H, linear or branched $C_1$-$C_{18}$ alkyl, linear or branched $C_2$-$C_{18}$ alkenyl, linear or branched $C_2$-$C_{18}$ alkynyl, F, Cl, Br, I, $NO_2$, CN, and OH;

b) unsaturated residues of General Formula VI:

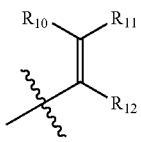

VI where $R_{10}$, $R_{11}$, and $R_{12}$ are independently chosen from the group consisting of H, F, Br, Cl, I, CN, $NO_2$, $COOR_{13}$, or $CON(R_{13})_2$, where $R_{13}$ is H or linear or branched $C_1$-$C_{18}$ alkyl and the residues $R_{10}$ and/or $R_{11}$ can be arranged both in (E) and also in (Z) conformation;

c) unsaturated residues of general formula (VII),

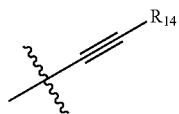

VII where $R_{14}$ is chosen from the group consisting of H, halogens (F, Cl, Br, and/or I), $Si(CH_3)_3$, primary, secondary, or tertiary amine or primary, secondary, or tertiary aminomethyl; or d) a residue chosen from the group of compounds of general formulas VIII-X

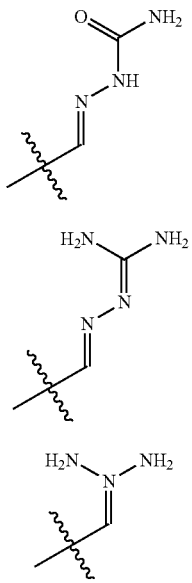

VIII

IX

X e) CHO, $COOR_{13}$, $CH_2OR_{13}$, $CON(R_{13})_2$, or 1,2,3-triazol-4-yl; and $R_3$ is chosen from the group consisting of H, linear or branched $C_1$-$C_{18}$ alkyl, linear or branched $C_2$-$C_{18}$ alkenyl, $C_5$-$C_8$ cycloalkyl, $C_5$-$C_8$ cycloalkenyl, unsubstituted or substituted benzyl, or benzoyl and/or a residue of General Formula XI:

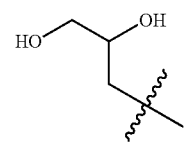

XI with the stipulation that the following compounds are excluded:

$R_1$=H, $R_2$=phenyl, $R_3$=ethyl and $R_4$=H;
$R_1$=H, $R_2$=2-hydroxy-3-methylphenyl;
$R_3$=ethyl, $R_4$=H;
$R_1$=H, $R_2$=4-methoxyphenyl, $R_3$=1-fluorovinyl and $R_4$=H.

If one or more of the residues $R_1$, $R_2$, $R_3$, or X has a chiral center, both the pure enantiomers and their racemates are included within the scope of this invention.

For residues $R_1$ and/or $R_4$ independently, the unsubstituted or substituted aromatic residues are preferably chosen from the group consisting of methyl, phenyl, mono-, di-, tri-, tetra-, or pentahalophenyl, especially 4-fluorophenyl, 2,6-difluorophenyl, 3,4-difluorophenyl, or perfluorophenyl, mono-, di-, or tri-$C_1$-$C_{18}$ alkoxyphenyl, especially 4-methoxyphenyl or 3,4,5-trimethoxyphenyl, mono-, di-, or trinitrophenyl, especially 4-nitrophenyl, or vinyl.

Preferably, $R_2$ is chosen from the group consisting of:

a) methyl, ethyl, propyl, 1,2-dichloro-2-hydroxyethyl, 1,2-dibromo-2-hydroxyethyl, 1,2-diiodo-2-hydroxyethyl;

b) (E)-2-chlorovinyl, (E)-2-bromovinyl, (E)-2-iodovinyl, 2,2-dibromovinyl, (E)-2-cyanovinyl, 2,2-dicyanovinyl, (E)-2-nitrovinyl, 2,2-dinitrovinyl, (E)-2-carboxyvinyl, (E)-2-cyano-2-carboxyvinyl, vinyl (E)-2-carboxy-$C_1$-$C_8$ alkyl ester, vinyl (E)-2-cyano-2-carboxy-$C_1$-$C_8$ alkyl ester, vinyl (E)-2-carboxylic acid amide, vinyl (E)-2-cyano-2-carboxylic acid amide, vinyl (E)-2-carboxylic acid $C_1$-$C_8$ alkylamide, vinyl (E)-2-cyano-2-carboxylic acid $C_1$-$C_8$ alkylamide, and the relevant (Z) isomers; or c) ethynyl, bromoethynyl, trimethylsilylethynyl.

It is further preferred that the $R_{14}$ is independently chosen from the group consisting of piperidino, piperazino, morpholino, piperidinomethyl, piperazinomethyl, and morpholinomethyl.

Preferably, the compounds in accordance with the invention are chosen from the group consisting of:

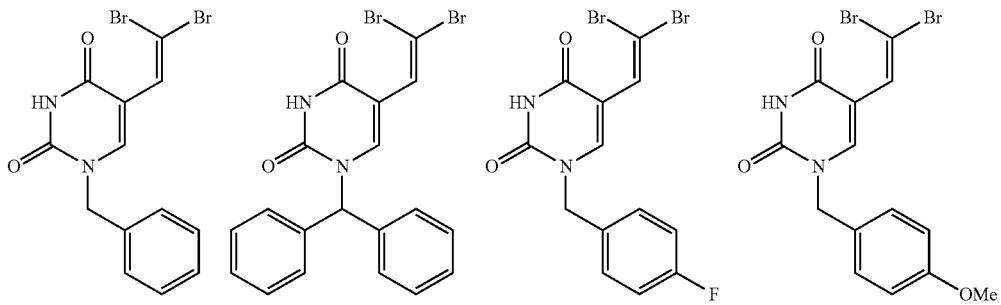

-continued
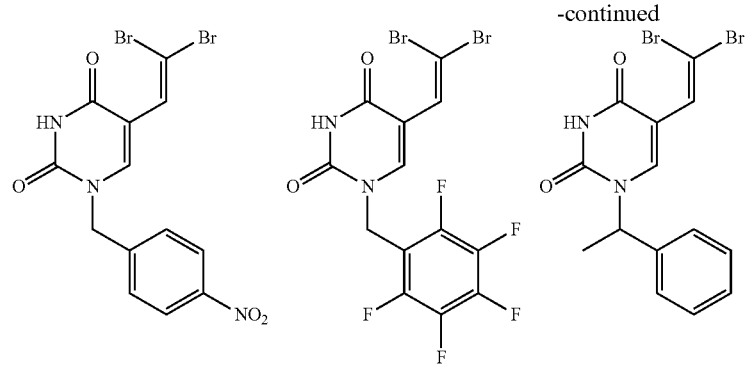
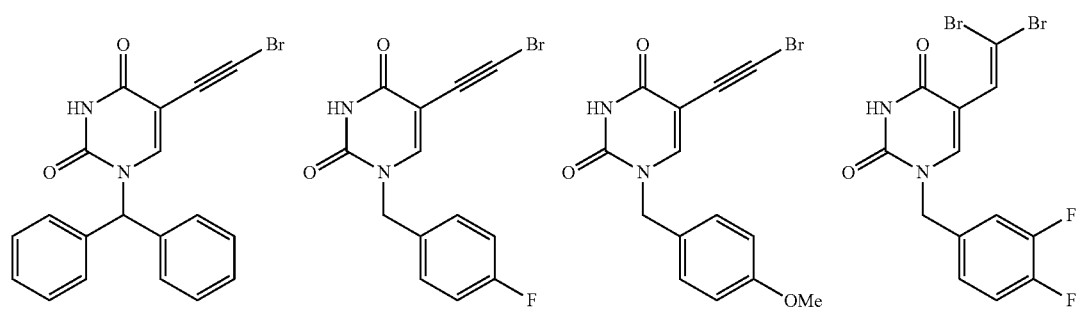
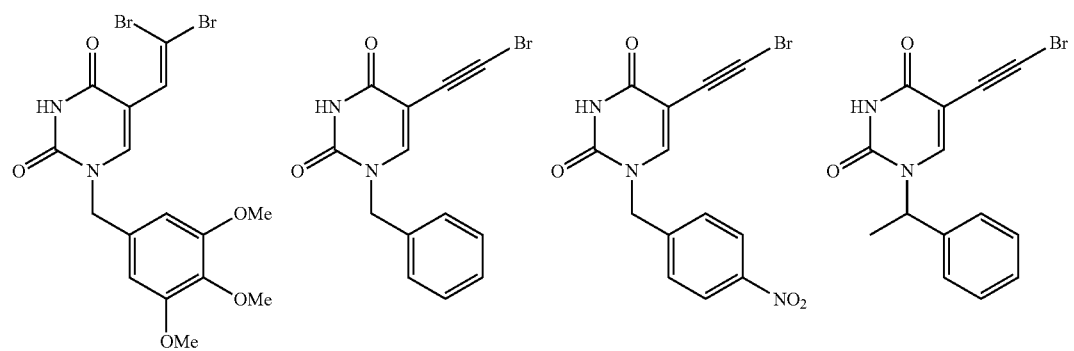
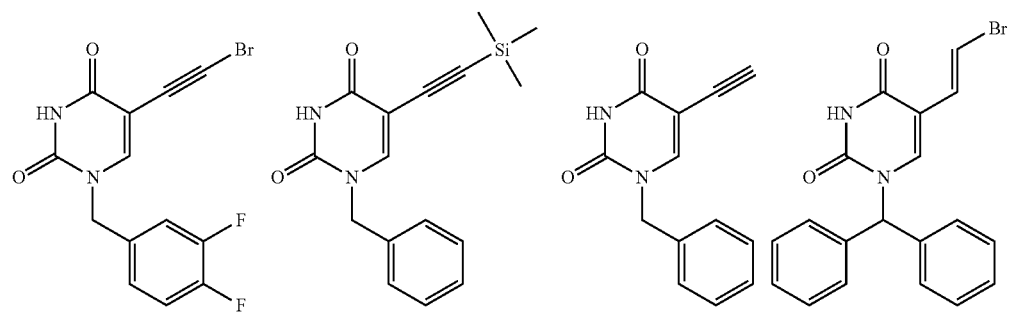
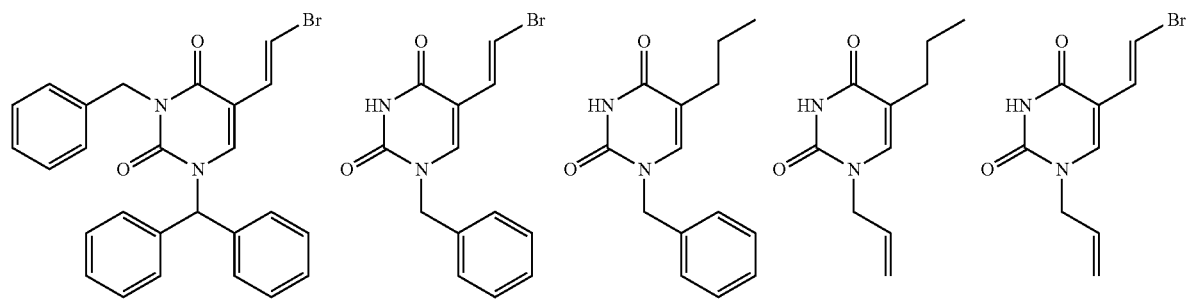

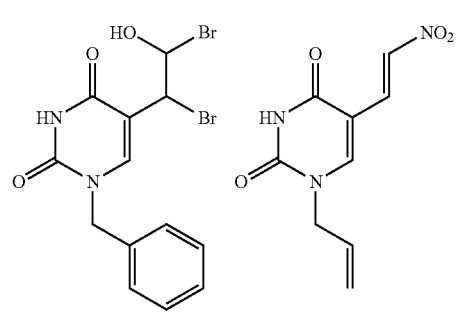
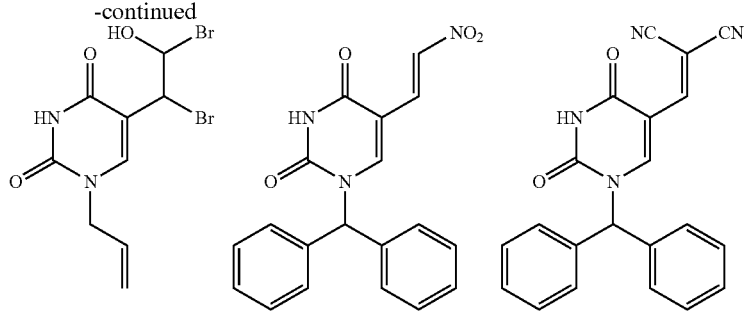
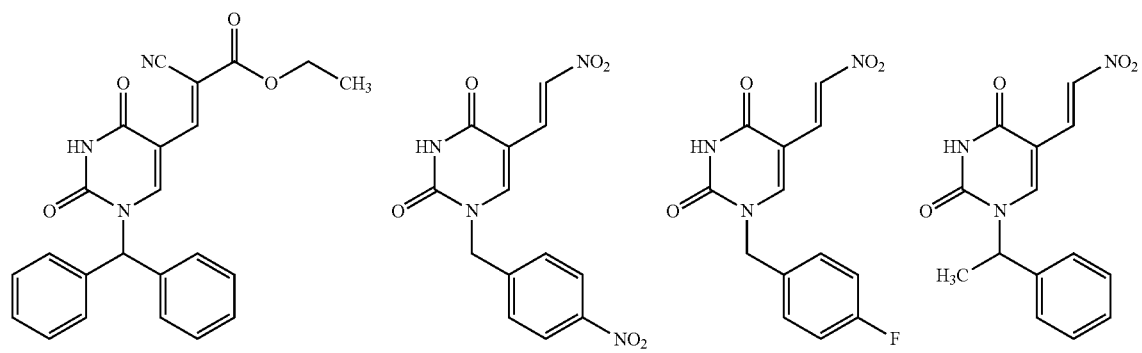
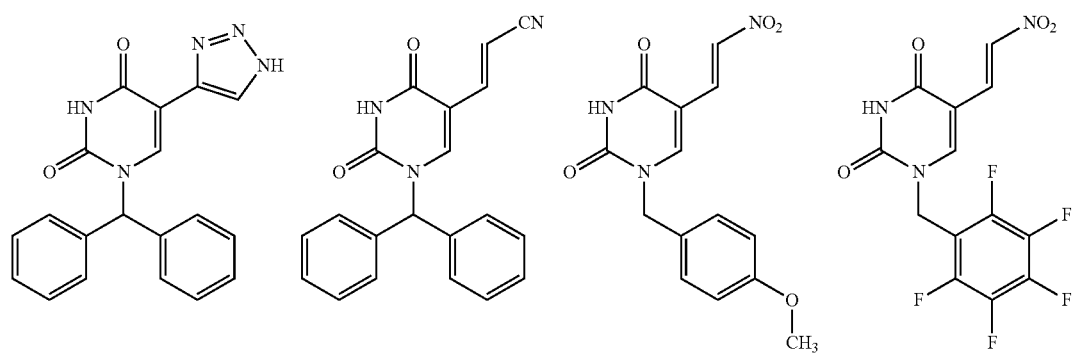
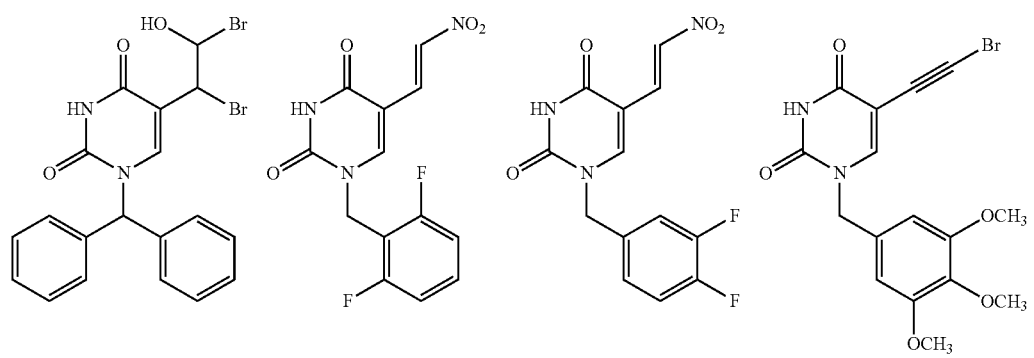

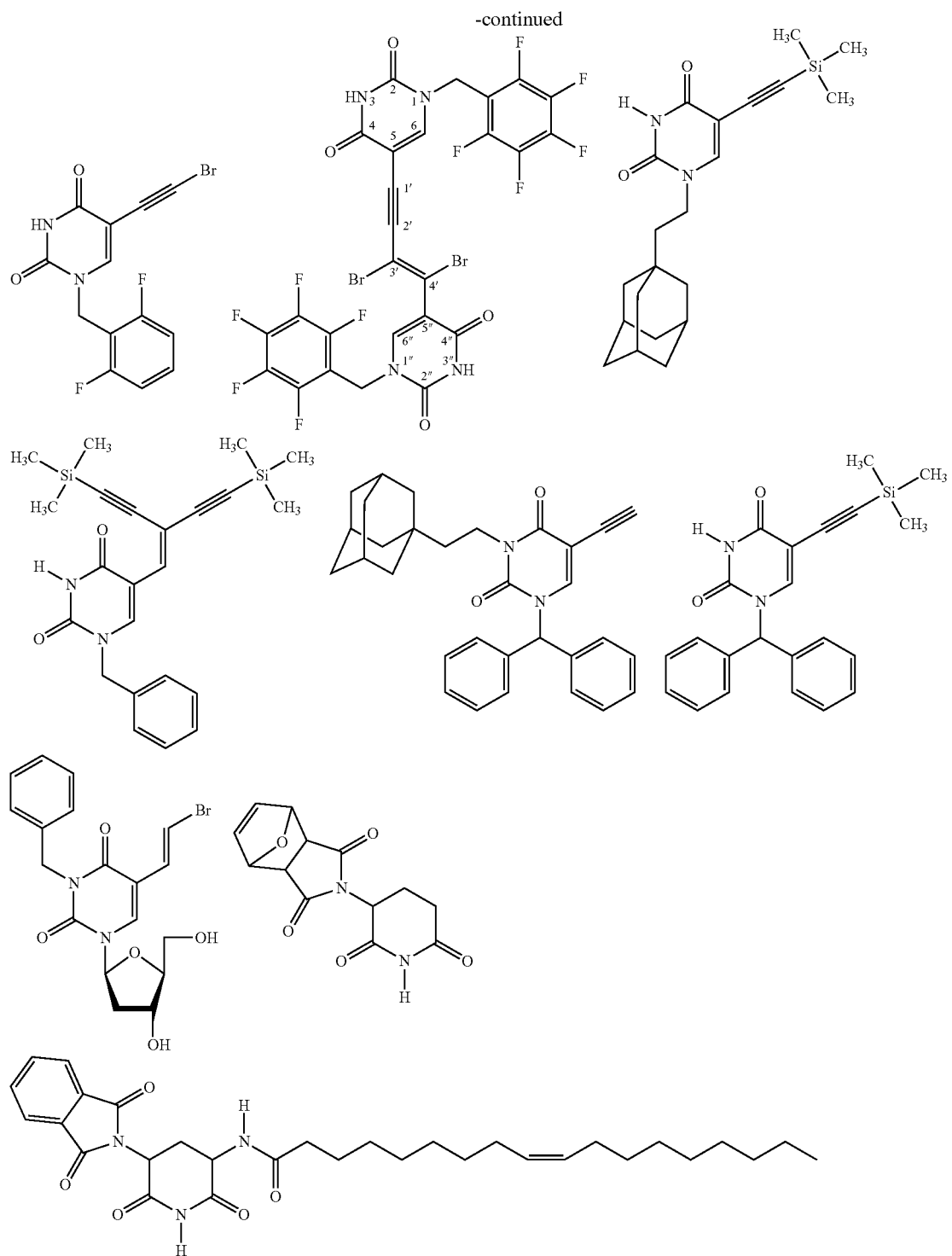

-continued

In accordance with the invention, the just described uracil derivatives are also made available for the first time for use as therapeutic agents.

They are preferably used together with at least one cytostatic agent in a joint formulation or in separate formulations.

In accordance with the invention, the use of the above-described uracil derivatives and at least one cytostatic is made available for suppression or reduction of resistance formation in cytostatic treatment.

The object of the invention is to be described in detail by means of the following examples and figures, without wishing to limit it to the particular embodiments described here.

BRIEF DESCRIPTION OF THE DRAWINGS

FIGS. 1-3 show the effect of compounds in accordance with the invention (in accordance with Examples 1-24, where the individual compounds are indicated by letters A through Y) in combination with mitomycin C (MMC) in a comparison with the administration of MMC by itself or the administration of MMC with BVDU, on the cell count of AH13r cells over time. AH13r cells were exposed to rising doses of the cytostatic MMC. One can see from all of the figures that the effect of MMC together with the compounds in accordance with the invention is clearly greater than MMC and BVDU.

DETAILED DESCRIPTION OF THE INVENTION

Examples

1) General Information

Figure 1A:
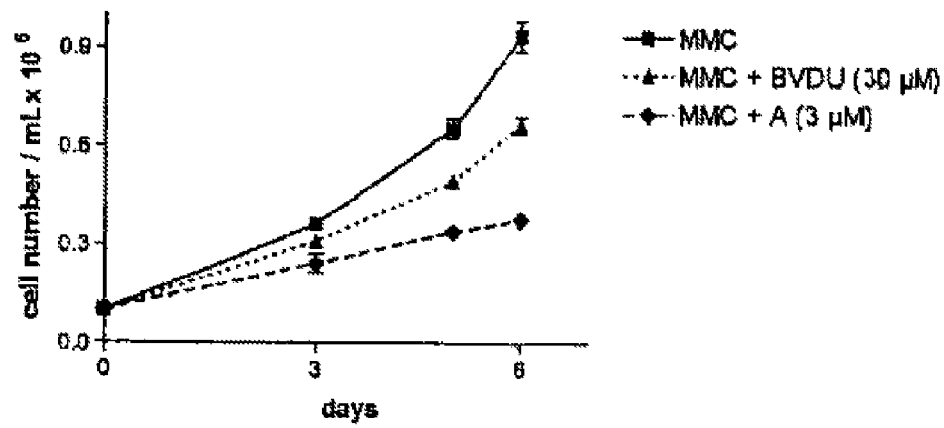
FIG. 1A depicts the effect of the combination of mitomycin C (MMC) and compound A on the cell count of AH13r cells as a function of time.
Figure 1B:
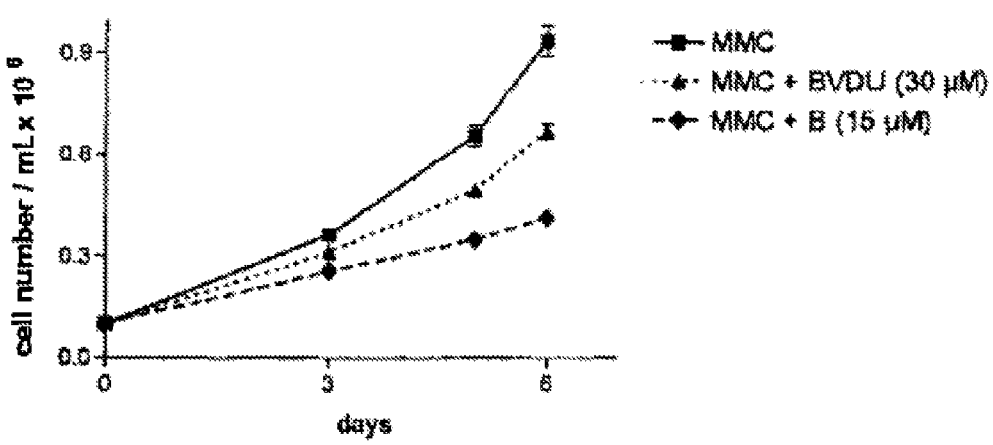
FIG. 1B depicts the effect of the combination of MMC and compound B on the cell count of AH13r cells as a function of time.
Figure 1C:
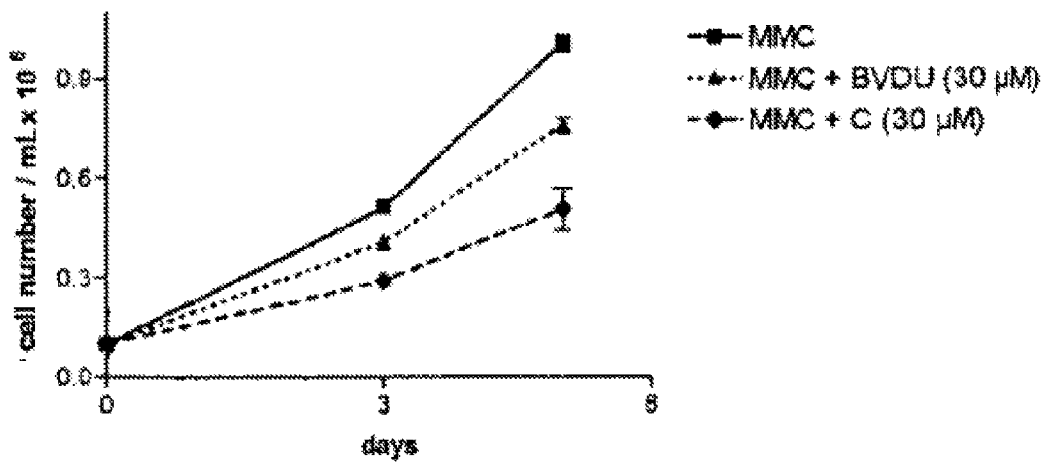
FIG. 1C depicts the effect of the combination of MMC and compound C on the cell count of AH13r cells as a function of time.
Figure 1D:
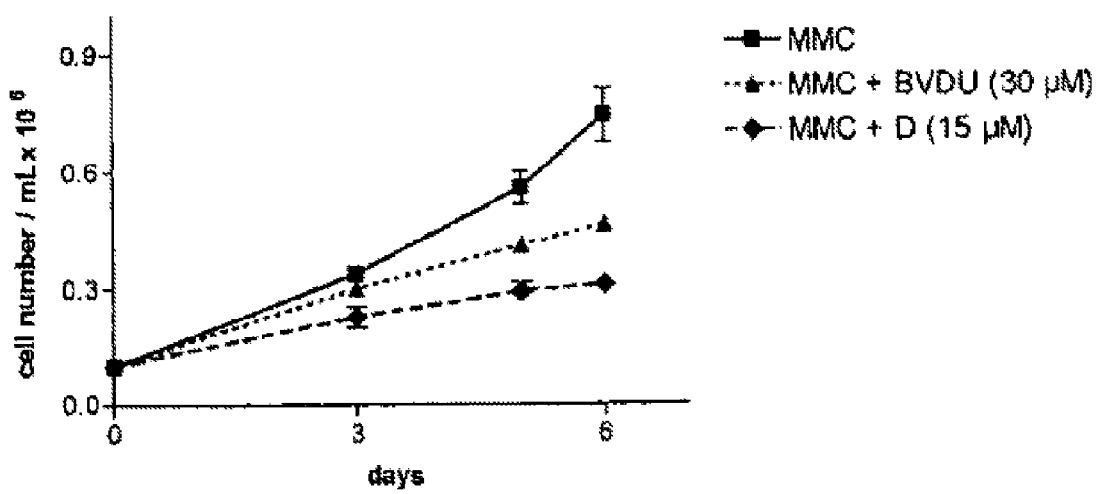
FIG. 1D depicts the effect of the combination of MMC and compound D on the cell count of AH13r cells as a function of time.
Figure 1E:
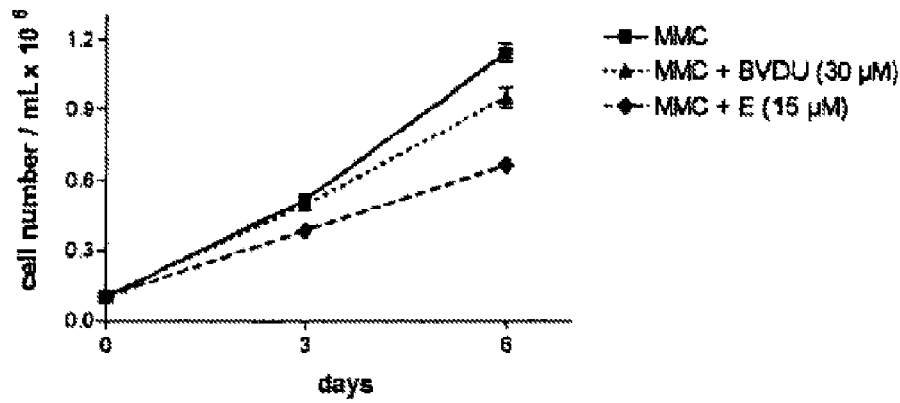
FIG. 1E depicts the effect of the combination of MMC and compound E on the cell count of AH13r cells as a function of time.
Figure 1F:
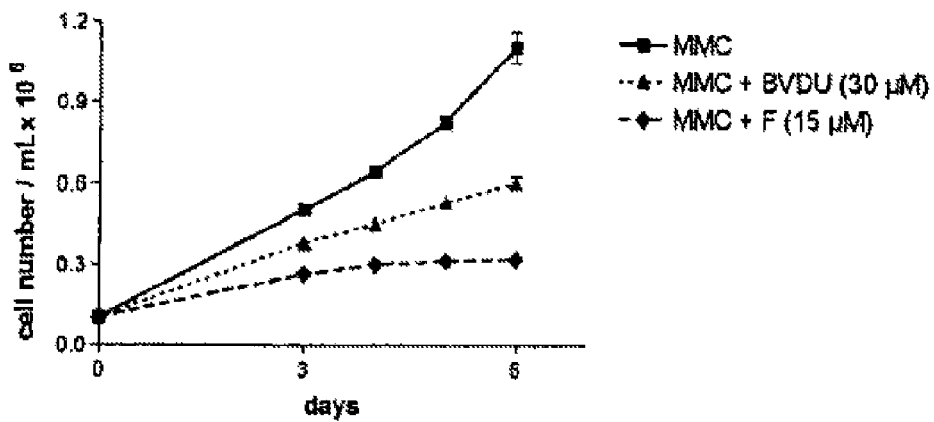
FIG. 1F depicts the effect of the combination of MMC and compound F on the cell count of AH13r cells as a function of time.
Figure 1G:
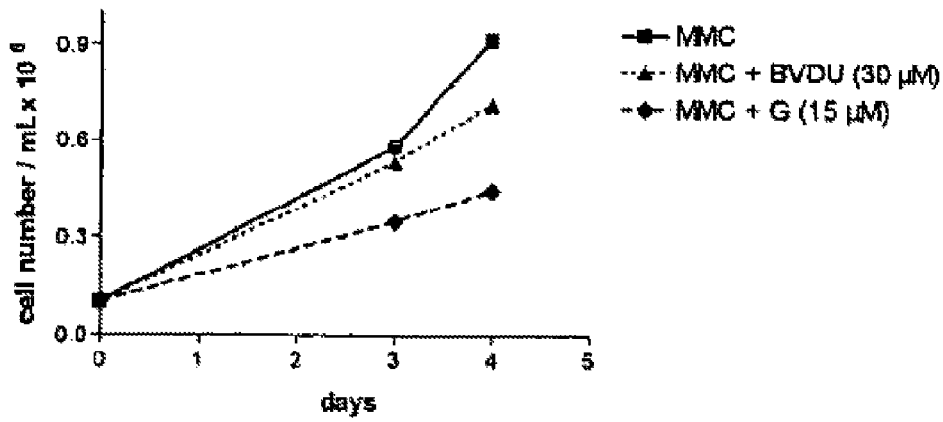
FIG. 1G depicts the effect of the combination of MMC and compound G on the cell count of AH13r cells as a function of time.
Figure 1H:
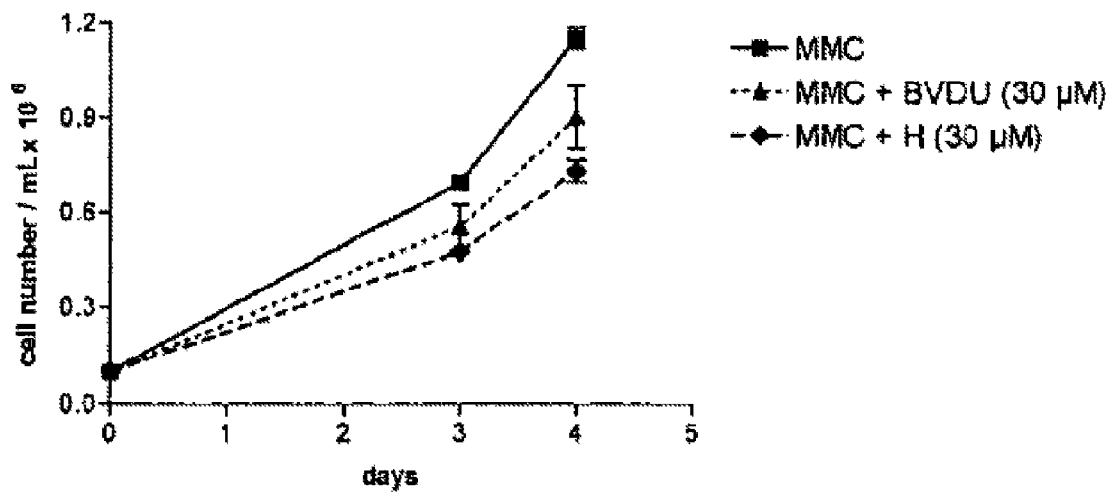
FIG. 1H depicts the effect of the combination of MMC and compound H on the cell count of AH13r cells as a function of time.
Figure 2A:
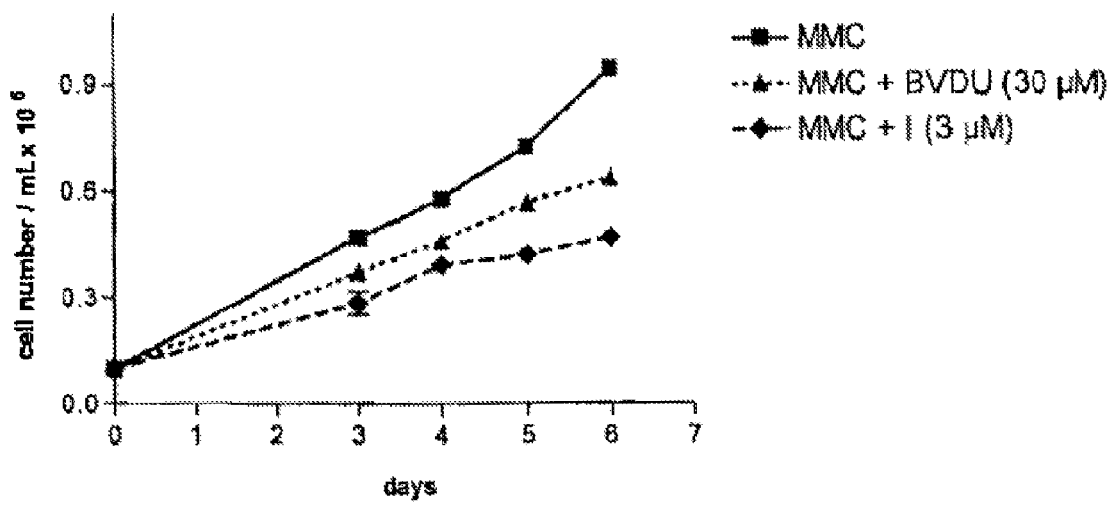
FIG. 2A depicts the effect of the combination of MMC and compound I on the cell count of AH13r cells as a function of time.
Figure 2B:
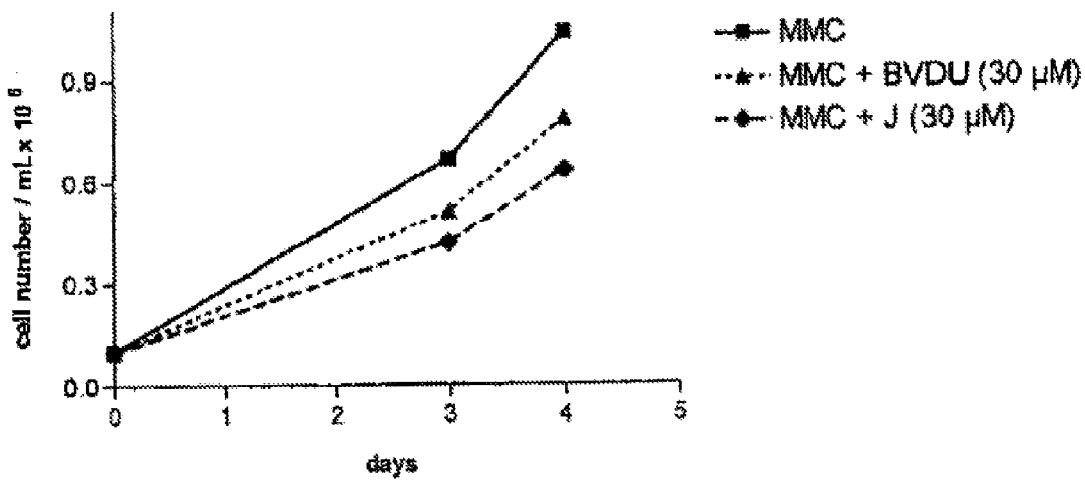
FIG. 2B depicts the effect of the combination of MMC and compound J on the cell count of AH13r cells as a function of time.
Figure 2C:
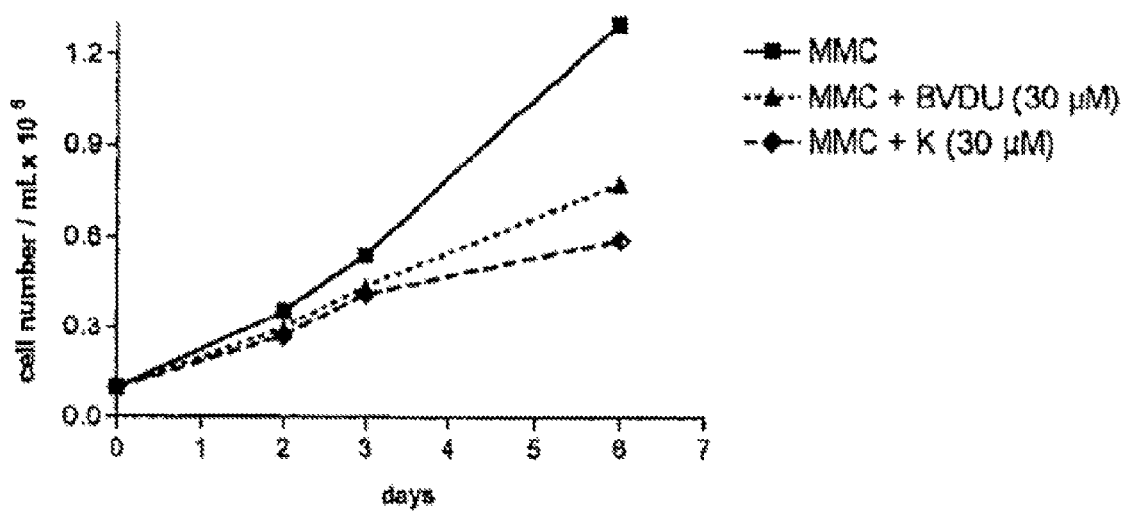
FIG. 2C depicts the effect of the combination of MMC and compound K on the cell count of AH13r cells as a function of time.
Figure 2D:
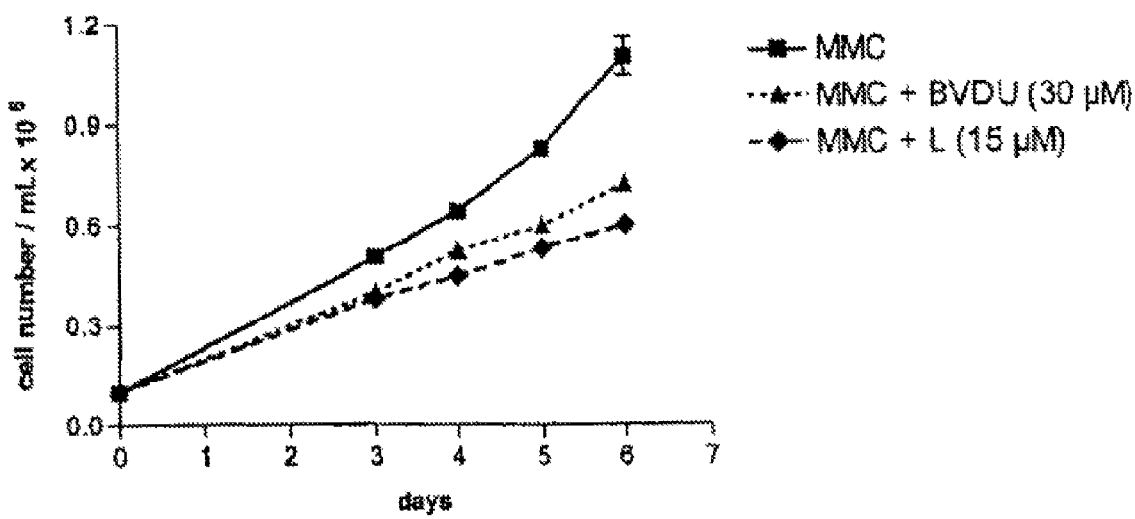
FIG. 2D depicts the effect of the combination of MMC and compound L on the cell count of AH13r cells as a function of time.
Figure 2E:
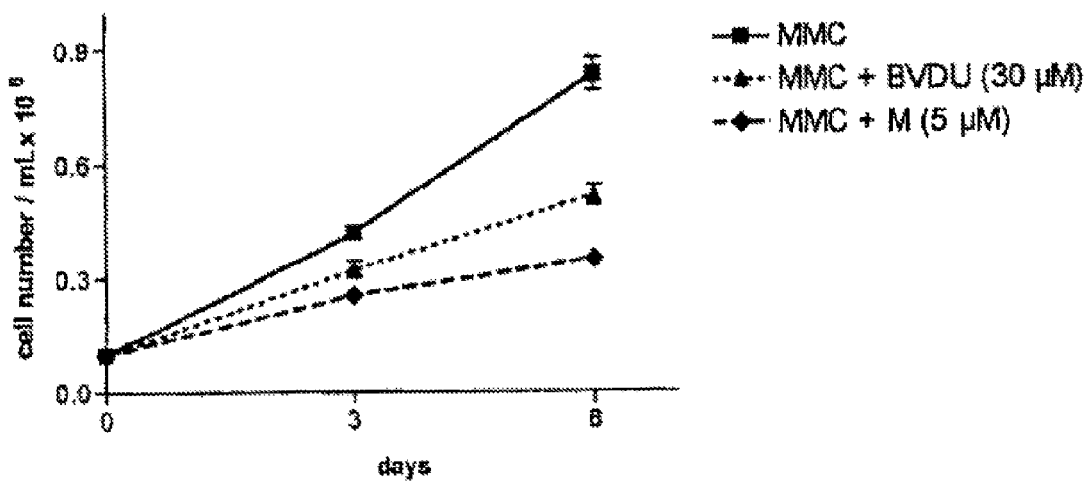
FIG. 2E depicts the effect of the combination of MMC and compound M on the cell count of AH13r cells as a function of time.
Figure 2F:
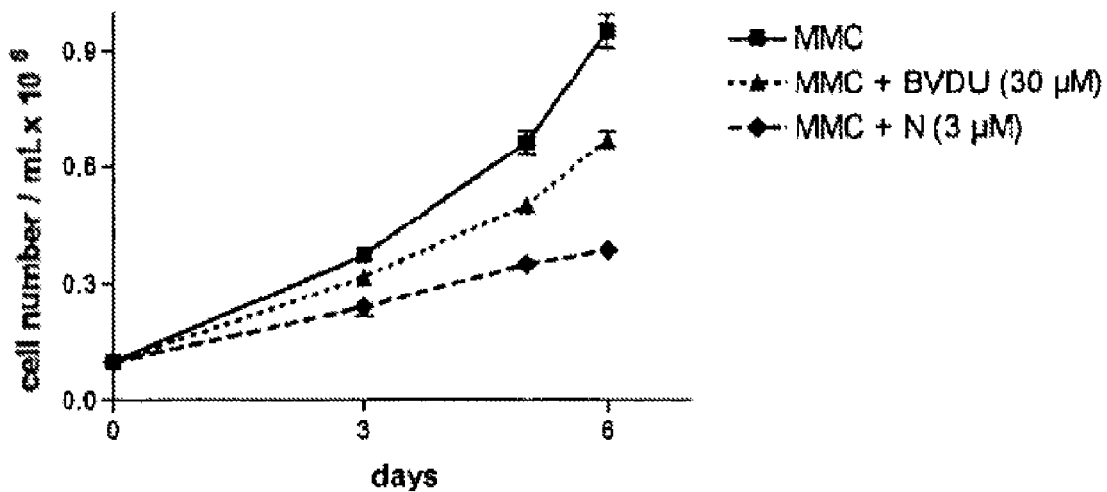
FIG. 2F depicts the effect of the combination of MMC and compound N on the cell count of AH13r cells as a function of time.
Figure 2G:
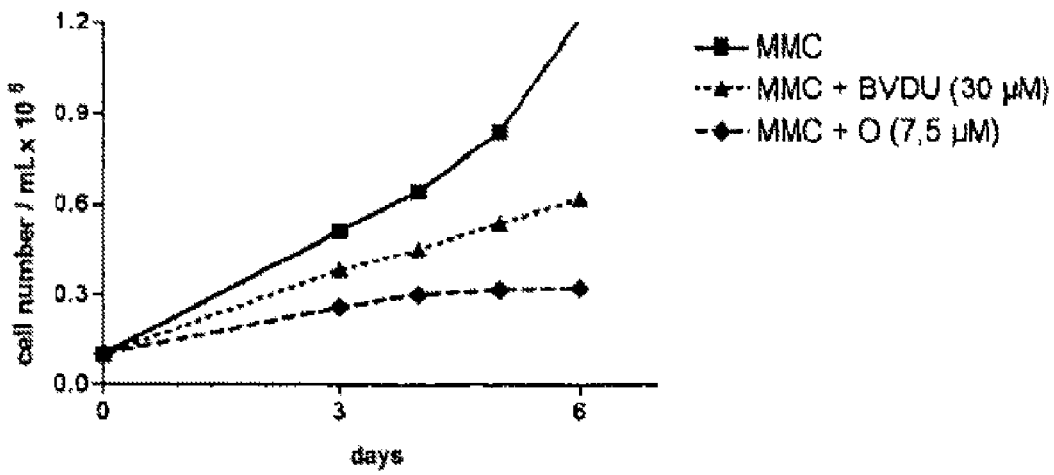
FIG. 2G depicts the effect of the combination of MMC and compound O on the cell count of AH13r cells as a function of time.
Figure 2H:
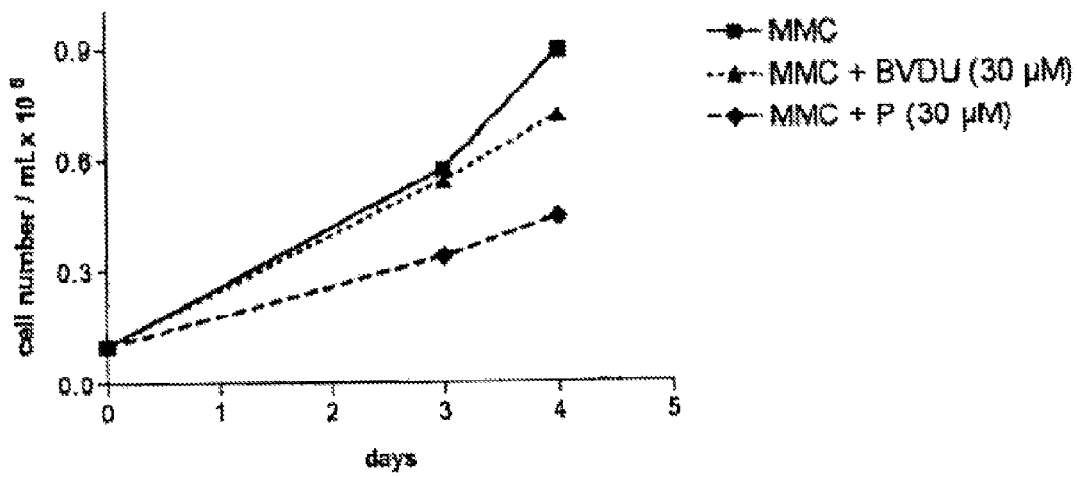
FIG. 2H depicts the effect of the combination of MMC and compound P on the cell count of AH13r cells as a function of time.
Figure 3A:
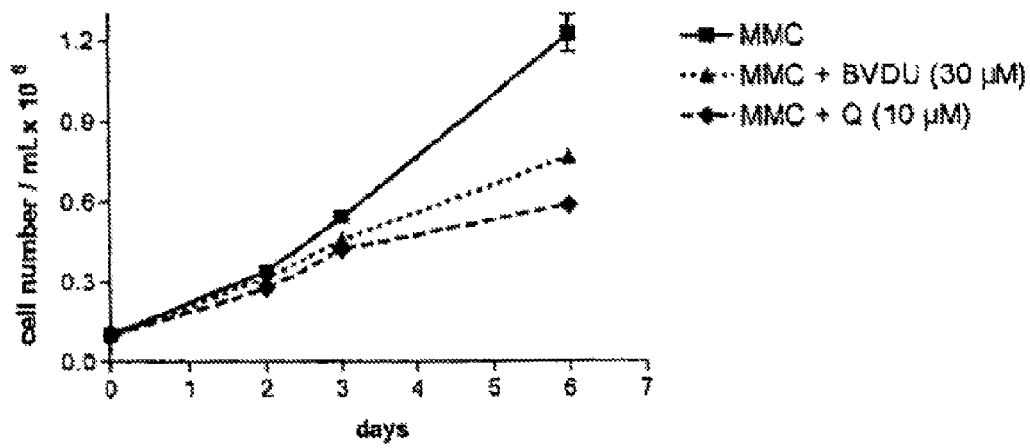
FIG. 3A depicts the effect of the combination of MMC and compound Q on the cell count of AH13r cells as a function of time.
Figure 3B:
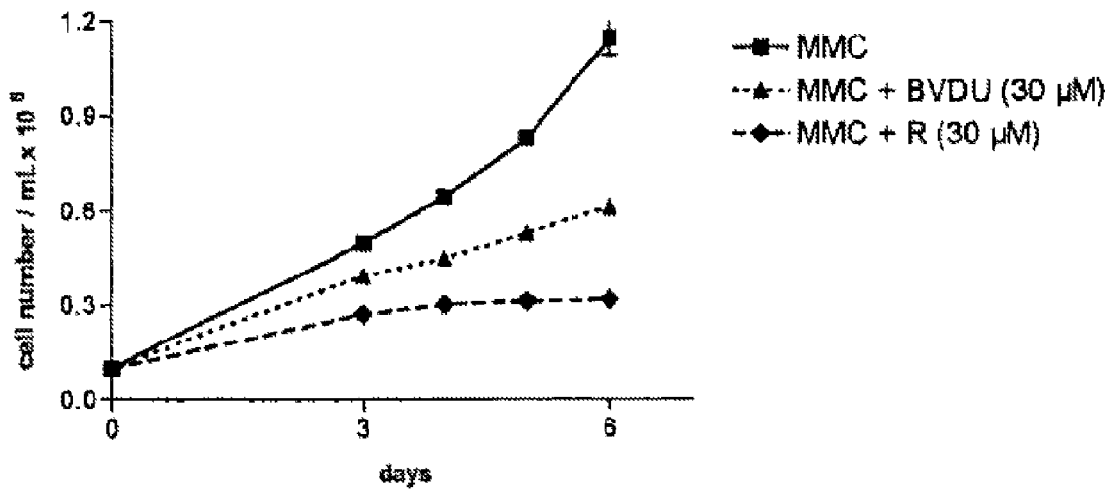
FIG. 3B depicts the effect of the combination of MMC and compound R on the cell count of AH13r cells as a function of time.
Figure 3C:
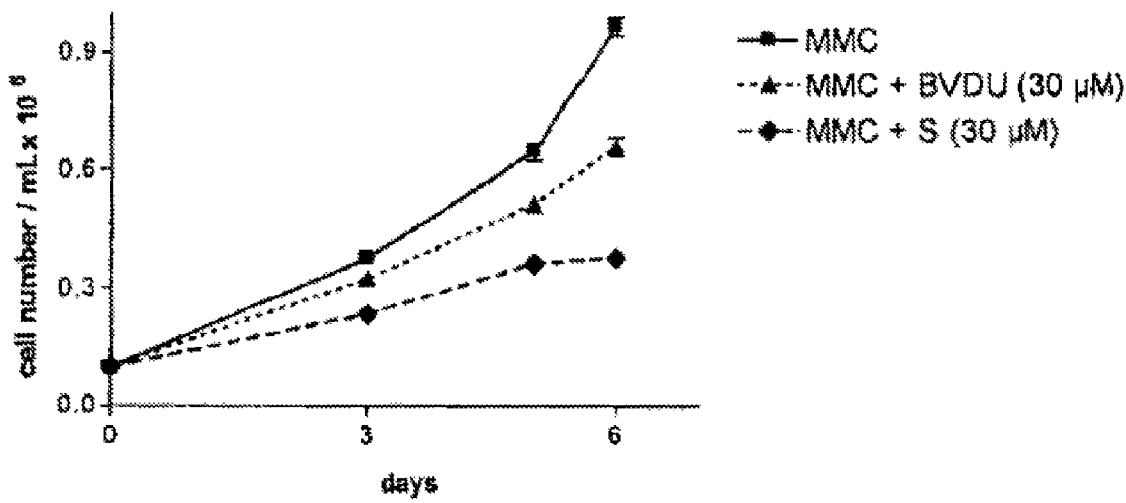
FIG. 3C depicts the effect of the combination of MMC and compound S on the cell count of AH13r cells as a function of time.
Figure 3D:
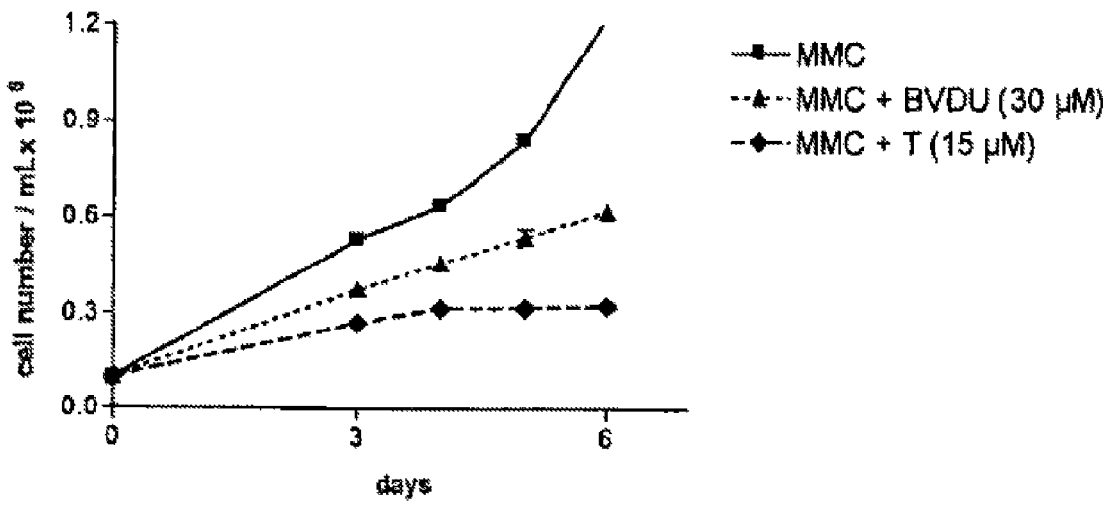
FIG. 3D depicts the effect of the combination of MMC and compound T on the cell count of AH13r cells as a function of time.
Figure 3E:
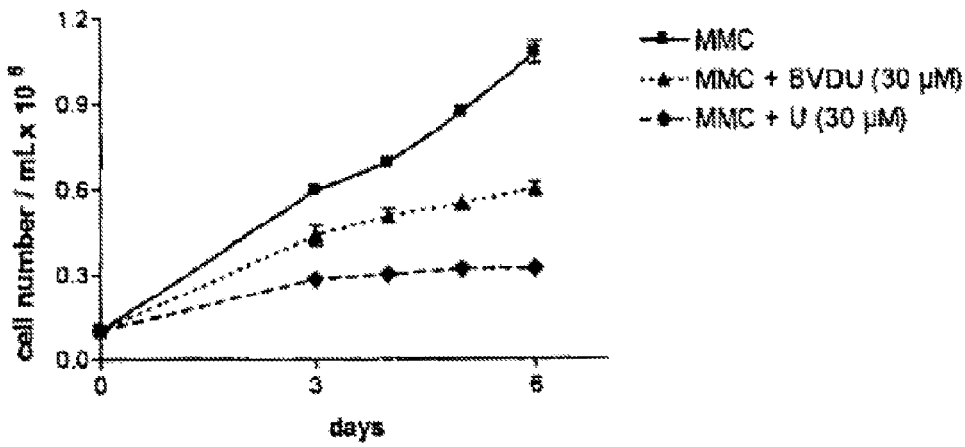
FIG. 3E depicts the effect of the combination of MMC and compound U on the cell count of AH13r cells as a function of time.
Figure 3F:
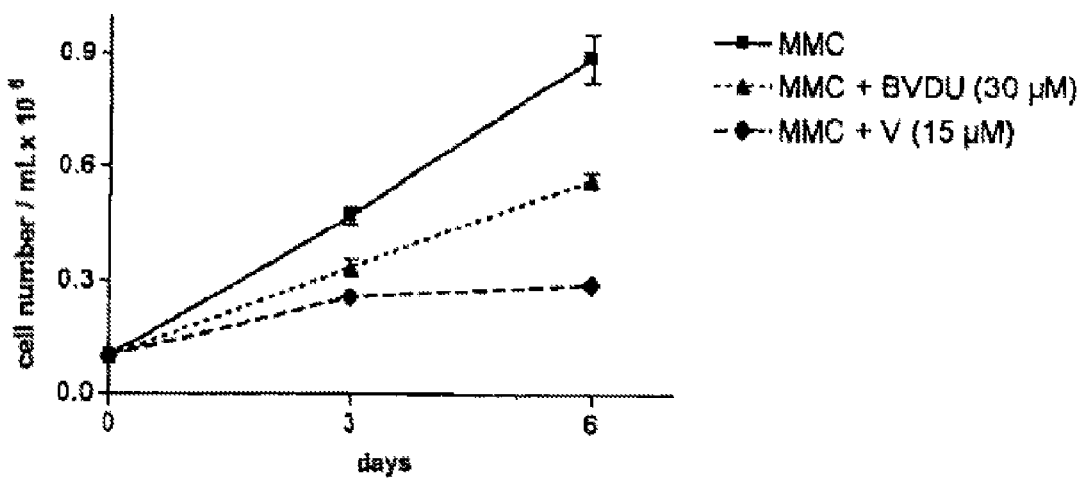
FIG. 3F depicts the effect of the combination of MMC and compound V on the cell count of AH13r cells as a function of time.
Figure 3G:
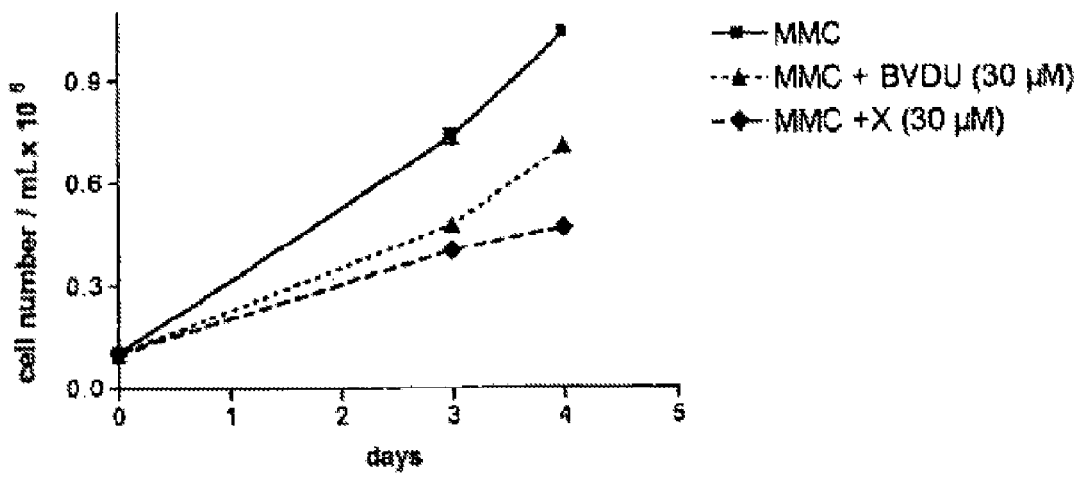
FIG. 3G depicts the effect of the combination of MMC and compound X on the cell count of AH13r cells as a function of time.
Figure 3H:
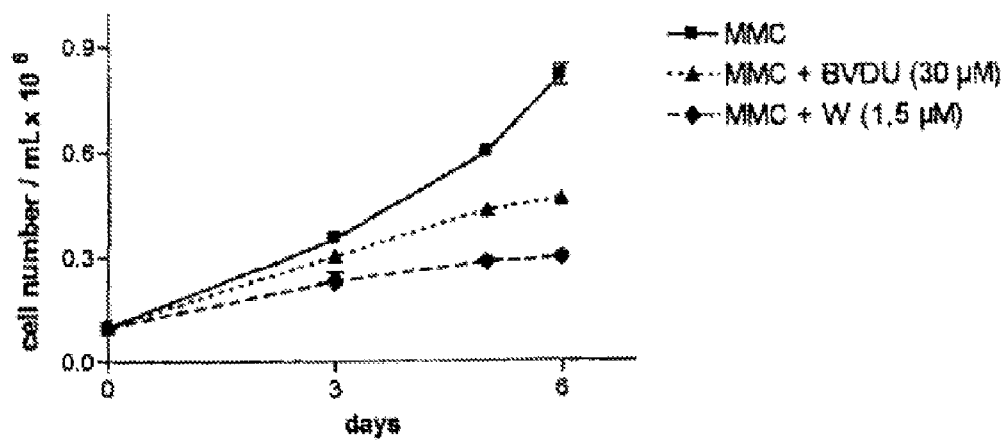
FIG. 3H depicts the effect of the combination of MMC and compound W on the cell count of AH13r cells as a function of time.
Figure 3I:
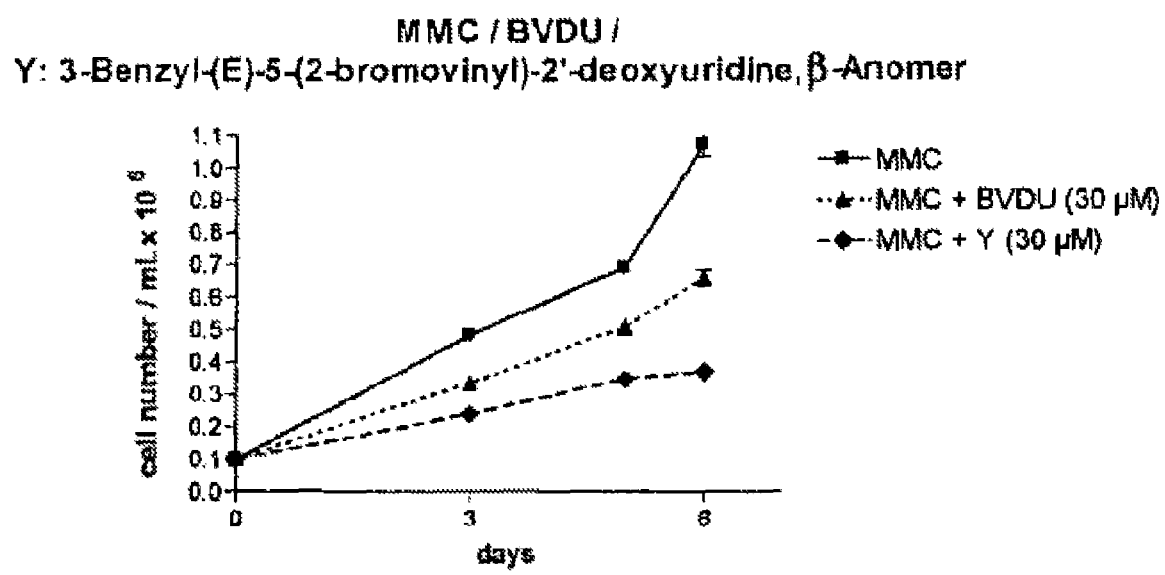
FIG. 3I depicts the effect of the combination of MMC and compound Y on the cell count of AH13r cells as a function of time.

Melting points were determined on a Boëtius micro-hot plate microscope (VEB Nagema). The values are corrected.

IR spectra were acquired on a Perkin Elmer PC 16 FT-IR spectrometer with potassium bromide wafers.

A Varian Mercury 300 spectrometer ($^1$H: 300 MHz; $^{13}$C: 75 MHz; $^{19}$F: 282 MHz), a Bruker X400 ($^1$H: 400 MHz; $^{13}$C: 100 MHz), or a Bruker DRX 600 spectrometer ($^1$H: 600 MHz; $^{13}$C: 150 MHz) were used to acquire the $^1$H and $^{13}$C NMR spectra. The solvent that was used in each case served as the internal standard for the chemical shift δ, which is given in ppm. Trifluoroacetic acid was used as reference in the case of the $^{19}$F NMR spectra. Unless otherwise specified, DMSO-d6 was used as solvent.

The EI mass spectra were acquired with a Variant MAT CH6 spectrometer (Thermo Electron Company) or with a VG ZAB-HSQ spectrometer (Waters). An Esquire 3000+ from Bruker Daltonics served for measurement of the ESI-LR mass spectra, and the ESI-HR measurements were made on a 7Tesla Apex™ II FT-ICR mass spectrometer from Bruker Daltonics (continuous flow injection by means of an injection pump, flow rate 120 µL/h, spray/drying gas: nitrogen). The mass/charge ratio and attribution are given in square brackets at the peaks of the mass spectra. The monoisotope mass peaks are given in the case of 5-bromoethynyluracil and 5-(2,2-dibromovinyl)uracil derivatives for an unambiguous attribution.

Silica gel 60, particle size 0.063-0.2 mm, from Merck was used for column chromatographic separations. Unless otherwise specified, a 3 cm×45 cm column containing 100 g silica gel fill was used. Silica gel 60 with particle size 0.040-0.063 mm from Merck was used for separation of compounds K and J. Analytical thin layer chromatography was carried out on silica gel DC films from Merck (silica gel 60 F254). Detection was done by interpretation in UV light (Desaga HP-UVIS 254 nm/366 nm).

The following solvent systems were used for thin layer and column chromatography:

| I | Toluene/acetone/methanol | 7:2:1 |
|---|---|---|
| II | Dichloromethane/methanol/ethanolic ammonia | 15:4:1 |
| III | Ethyl acetate/n-hexane | 6:4 |
| IV | Ethyl acetate/n-hexane | 7:3 |
| V | Ethyl acetate/methanol | 9:1 |

The following substances were synthesized in accordance with existing literature procedures:

5-bromoethinyluracil (1), 5-hydroxymethyluracil (2), 5-(2,2-dibromovinyl)uracil (3), 2-deoxy-3,5-di-O-(p-chlorobenzoyl)-D-ribofuranosyl chloride (4), 5-ethynyl uracil (5) and 5-trimethylsilylethynyluracil (6).

To ensure better comparability of the NMR data, the atoms of the compounds are in some cases numbered differently from the existing IUPAC nomenclature.

Example 1

1-Benzhydryl-3-benzyl-5-(2-bromovinyl)uracil (A)

(1-benzhydryl-3-benzyl-5-4E)-2-bromovinyl)pyrimidine-2,4(1H,3H)dione)

$C_{26}H_{21}BrN_2O_2$ Mw 473.37

0.96 g (2.5 mmol) 1-benzhydryl-BVU and 0.42 g (3.0 mmol) $K_2CO_3$ are mixed in 8 mL DMF under a protective gas atmosphere. 0.45 mL (3.75 mmol) benzyl bromide is added to the suspension and stirred for 12 h at room temperature (control of reaction with DC, solvent hexane/ethyl acetate=5/1). The batch is mixed with 30 mL ether and then washed several times in a separatory funnel. The organic phase is dried over Na2SO4 and then evaporated until dry.

Yield: 0.65 g (1.4 mmol, 56% of theory)

Melting point: 131° C.

$^1$H-NMR (DMSO-d6, δ [ppm]): 5.03 (s, 2H, CH2), 6.91 (d, 1H, =CHBr, $^3$JH—H=13.5 Hz), 7.02 (s, 1H, N—CH), 7.21-7.41 (m, 15 H, Ar) 7.26 (d, 1H, —CH=, $^3$JH—H=13.2 Hz), 7.70 (s, 1H, H 6)

$^{13}$C-NMR (DMSO-d6, δ [ppm]): 45.0 (CH2), 63.8 (N—CH), 108.0 (C 5), 109.9 (=CHBr), 127.9-129.6 (15C, Ar) 130.7 (—CH=), 137.4 (C 1', Benzyl), 138.3 (C1', Benzhydryl), 141.5 (C 6), 151.0 (C 2), 161.2 (C 4)

MS (ESI positive, acetone/MeOH) m/z: 495.06817 [M+Na]$^+$ (calculated for $C_{26}H_{21}BrN_2Na_2O_2^+$: 495.06786) 967.14686 [2M+Na]$^+$ (calculated for $C_{52}H_{42}Br_2N_4NaO_4^+$: 967.14650)

IR (KBr, ν [cm$^{-1}$]): 1660, 1703 (Lactam)

Example 2

1-Benzyl-5-(2-bromovinyl)uracil (B)

(1-Benzyl-54(E)-2-bromovinyl)pyrimidine-2,4(1H,3H)dione)

C13H11BrN2O2 Mw 307.15

0.43 g (2.0 mmol) 5-(2-bromovinyl)uracil (2) is suspended in 20 mL absolute dichloroethane. Then the batch is covered with argon and 1.2 mL (5.0 mmol) BSA, and a few drops of CTMS are added while stirring. After a clear solution is formed, 0.28 mL (2.4 mmol) benzyl bromide and a catalytic quantity of iodine are added, and the mixture is heated for 24 h at reflux. Then the batch is purified by column chromatography on silica gel (ethyl acetate/hexane=7/3).

Yield: 0.11 g (0.36 mmol, 18% of theory)

Melting point: 183° C.

$^1$H-NMR (DMSO-d6), δ [ppm]): 4.86 (s, 2H, CH2), 6.79 (d, 1H, =CHBr, $^3$JH—H=13.2 Hz), 7.24 (d, 1H, —CH=, $^3$JH—H=13.8 Hz), 7.28-7.35 (m, 5H, Ar), 8.04 (s, 1H, H 6), 11.60 (s, 1H, NH)

$^{13}$C-NMR (DMSO-d6, δ [ppm]): 51.5 (CH2), 107.2 (C 5), 110.3 (=CHBr), 128.2 (C 2' and C 6'), 128.5 (C 4'), 129.4 (C 3' and C 5'), 130.2 (—CH=), 137.1 (C 1'), 145.2 (C 6), 150.5 (C 2), 162.8 (C 4)

MS (ESI positive, acetone/MeOH) m/z: 328.98984 [M+Na]$^+$ (calculated for $C_{13}H_{11}BrN_2NaO_2^+$: 328.98961) 634.98966 [2M+Na]$^+$ (calculated for $C_{26}H_{22}Br_2N_4NaO_4^+$: 634.99000)

IR (KBr, ν [cm$^{-1}$]): 1678, 1699 (Lactam)

Example 3

1-Allyl-5-(2-bromovinyl)uracil (C)

(1-Allyl-54(E)-2-bromovinyl)pyrimidine-2,4(1H,3R)dione)

C9H9BrN2O2 Mw 257.09

0.43 g (2.0 mmol) 5-(2-bromovinyl)uracil (2) is suspended in 20 mL absolute dichloroethane, the batch is covered with argon and 1.2 mL (5.0 mmol) BSA, and a few drops of CTMS are added while stirring. After about 30 min a clear solution forms, 0.21 mL (2.4 mmol) allyl bromide and a catalytic quantity of iodine are added, and the mixture is heated at reflux for 24 h. Then the batch is poured onto silica gel and processed by column chromatography with ethyl acetate/hexane=7/3.

Yield: 0.13 g (0.5 mmol, 20% of theory)

Melting point: 137° C.

$^1$H-NMR (DMSO-d6, δ [ppm]): 4.28 (d, 2H, H 1'), 5.11-5.21 (m, 2H, H 3'), 5.84-5.93 (m, 1H, H 2'), 6.80 (d, 1H, =CHBr, $^3$JH—H=13.8 Hz), 7.24 (d, 1H, —CH=, $^3$JH—H=13.5 Hz), 7.85 (s, 1H, H 6), 11.56 (s, 1H, NH)

$^{13}$C-NMR (DMSO-d6, δ [ppm]): 50.2 (C 1'), 107.0 (C 5), 110.1 (=CHBr), 118.4 (C 3'), 130.2 (—CH=), 133.4 (C 2'), 145.1 (C 6), 150.3 (C 2), 162.8 (C 4)

MS (ESI positive, acetone/MeOH) m/z: 278.97415 [M+Na]$^+$ (calculated for $C_9H_9BrN_2NaO_2^+$: 278.97396) 534.95863 [2M+Na]$^+$ (calculated for $C_{18}H_{18}Br_2N_4NaO_4^+$: 534.95870)

IR (KBr, ν [cm$^{-1}$]): 1678, 1695 (lactam)

Example 4

1-Benzyl-5-bromoethynyluracil (D)

C13H9BrN2O2 Mw 305.13

The reaction takes place by analogy with the general method of preparation for benzyl-substituted uracil derivatives from (1) and benzyl bromide.

Yield: 150 mg (49% of theory)

Melting point: 162-165° C.

$^1$H-NMR (δ [ppm]): 4.85 (s, 2H, N—CH2-); 7.28-7.37 (m, 5H, Aromatic); 8.31 (s, 1H, H-6); 11.69 (s, 1H, H-6); 11.69 (s, 1H, H-6); 11.69 (s, 1H, —NH)

$^{13}$C-NMR (δ [ppm]): 51.6 (N—CH2-); 55.5 (=C—Br); 73.2 (—C=); 98.2 (C-5); 128.3 (C-2' and C-6'); 128.5 (C-4'); 129.4 (C-3' and C-5'); 137.0 (C-1'); 150.6 (C-6); 150.6 (C-2); 162.7 (C-4)

MS (ESI positive, methanol) m/z: 326.97426 [M+Na]$^+$ (calculated for $C_{13}H_9BrN_2NaO_2^+$: 326.97396) 630.95910 [2M+Na]$^+$ (calculated for $C_{26}H_{18}Br_2N_4NaO_4^+$: 630.95870)

IR (KBr, ν [cm$^{-1}$]): 1682 (Lactam); 2202 (Ethynyl)

Example 5

2-((1-Benzhydryl-1,2,3,4-2,4-dioxopyrimidine-5-yl)methylene)malononitrile (E)

$C_{21}H_{14}N_4O_2$ Mw 354.37

0.38 g (2.0 mmol) 24(1,2,3,4-tetrahydro-2,4-dioxopyrimidin-5-yl)methylene)malononitrile is suspended in 20 mL acetonitrile under an argon atmosphere. 1.2 mL (5.0 mmol) BSA and a few drops of CTMS are added and stirred for 15 min. 0.74 g (3.0 mmol) benzhydryl bromide and a spatula tip of iodine are added to the clear solution, and the mixture is heated for 12 h at reflux. The solvent is evaporated out and the viscous residue is taken up in hexane. Then the organic phase is absorbed on silica gel and chromatographed with hexane/ethyl acetate=3/2.

Yield: 0.22 g (0.6 mmol, 30% of theory)
Melting point: 178° C.
$^1$H-NMR (DMSO-d6) δ [ppm]): 6.99 (s, 1H, N—CH), 7.21-7.41 (m, 10 H, Ar), 7.91 (s, 1H, —CH═), 8.30 (s, 1H, H 6), 12.17 (s, 1H, NH)
$^{13}$C-NMR (DMSO-d6, δ [ppm]): 64.0 (N—CH), 78.1 (═CH(CN)2), 107.9 (C 5), 113.8 (CN), 115.5 (CN), 129.2 (C4'), 129.3 (C 2' and C 6'), 129.7 (C 3' and C 5'), 137.6 (C 1'), 149.1 (C 6), 150.1 (—CH═), 153.1 (C 2), 160.9 (C 4)
MS (ESI positive, acetone) m/z: 377.10135 [M+Na]$^+$ (calculated for $C_{21}H_{14}N_4NaO_2^+$: 377.10090) 731.21242 [2M+Na]$^+$ (calculated for $C_{42}H_{28}N_8NaO_4^+$: 731.21257)
IR (KBr, ν [cm$^{-1}$]): 1695, 1724 (Lactam), 2228 (CN)

Example 6

1-Benzhydryl-5-(1H-1,2,3-triazol-4-yl)uracil (F)

C19H15N5O2 Mw 345.36
0.35 g (1.0 mmol) 1-benzhydryl-5-(2-nitrovinyl)uracil and 0.13 g (2.0 mmol) sodium azide are heated in 15 mL DMSO for 45 min at 90° C. on an oil bath. After the reaction is over, the solvent is evaporated out and the product is precipitated by adding 20 mL ice water. The precipitate is suctioned out sharply and washed with water.

Yield: 0.19 g (0.56 mmol, 56% of theory)
Melting point: 165° C.
$^1$H-NMR (DMSO-d6, δ [ppm]): 7.00 (s, 1H, N—CH), 7.20-7.43 (m, 10 H, Ar) 7.81 (s, 1H, ═CHNH), 8.07 (s, 1H, H 6)
$^{13}$C-NMR (DMSO-d6, δ [ppm]): 62.0 (N—CH), 105.5 (C 5), 126.6 (═CNHN═), 128.3-129.0 (10C, Ar), 137.2 (N—C═C), 137.4 (C 6), 138.0 (C 1'), 150.4 (C 2), 161.4 (C 4)
MS (ESI positive, acetone) m/z: 368.11167 [M+Na]$^+$ (calculated for C19H15N5NaO2$^+$: 368.11180) 713.23393 [2M+Na]$^+$ (calculated for C38H30N10NaO4$^+$: 713.23437)
IR (KBr, ν [cm$^{-1}$]): 1685 (lactam)

Example 7

1-Benzhydryl-5-(2-cyanovinyl)uracil (G)

((2E)-3-(1-benzhydryl-1,2,3,4-tetrahydro-2,4-dioxopyrimidin-5-yl)acrylonitrile)

$C_{13}H_{11}BrN_2O_2$ Mw 329.36
0.33 g (2.0 mmol) 5-(2-cyanovinyl)uracil is suspended in 30 mL acetonitrile under an argon atmosphere and silylated while adding 1.2 mL (5.0 mmol) BSA and a few drops of CTMS. A clear solution has formed after 45 min and is mixed with 0.74 g (3.0 mmol) benzhydryl bromide and a catalytic quantity of iodine. The reaction mixture is heated at reflux for 8 h, the solvent is driven off in a vacuum, and the match is then mixed with 20 mL cold ethyl acetate. The resulting precipitate is suctioned out.

Yield: 0.09 g (0.3 mmol, 15% of theory)
Melting point: 261° C.
$^1$H-NMR (DMSO-d6, δ [ppm]): 6.54 (d, 1H, ═CHCN, $^3$JH—H=15.9 Hz), 6.96 (s, 1H, N—CH), 7.20-7.43 (m, 10 H, Ar), 7.25 (d, 1H, —CH═, $^3$JH—H=15.9 Hz), 7.85 (s, 1H, H 6), 11.86 (s, 1H, NH)
$^{13}$C-NMR (DMSO-d6, δ [ppm]): 62.0 (N—CH), 94.6 (═CHCN), 108.2 (C 5), 119.2 (CN), 128.3 (C 4'), 128.5 (C 2' and C 6'), 128.9 (C 3' and C 5'), 137.5 (C 1'), 144.5 (C 6), 146.9 (—CH═), 149.7 (C 2), 161.6 (C 4)
MS (ESI positive, acetone) m/z: 352.10553 [M+Na]$^+$ (calculated for $C_{20}H_{15}N_3NaO_2^+$: 352.10565) 681.22194 [2M+Na]$^+$ (calculated for $C_{40}H_{30}N_6NaO_4^+$: 681.22207)
IR (KBr, ν [cm$^{-1}$]): 1685, 1707 (Lactam), 2215 (CN)

Example 8

1-Allyl-5-(2,2-dibromovinyl)uracil (H)

C9H8Br2N2O2 Mw 335.98
300 mg (1 mmol) 5-(2,2-dibromovinyl)uracil are suspended in 40 mL absolute dichloroethane, mixed with 0.61 mL (2.5 mmol) BSA and a few drops of chlorotrimethylsilane, and stirred at room temperature until a clear solution is formed. Then 0.10 mL (1.2 mmol) allyl bromide and catalytic quantities of iodine are added, and the mixture is covered with argon. The batch is heated at reflux for 48 h, monitoring the course of the reaction by DC (solvent II). The solvent is evaporated out, the batch is absorbed on silica gel and purified by column chromatography (solvent III).

Yield: 260 mg (77% of theory)
Melting point: 154-156° C.
$^1$H-NMR (δ [ppm]): 4.35 (d, 2H, H-1'); 5.15-5.22 (m, 2H, H-3'); 5.85-5.94 (m, 1H, H-2'); 7.21 (s, 1H, —CH═CBr2); 8.10 (s, 1H, H-6); 11.65 (s, 1H, —NH)
$^{13}$C-NMR (δ [ppm]): 50.2 (C-1'); 89.7 (—CH═CBr2); 109.5 (C-5); 118.6 (C-3'); 129.0 (—CH═CBr2); 133.2 (C-2'); 144.5 (C-6); 150.4 (C-2); 162.5 (C-4)
MS (ESI positive, acetone) m/z: 356.88459 [M+Na]$^+$ (calculated for $C_9H_8Br_2N_2NaO_2^+$: 356.88447) 690.78036 [2M+Na]$^+$ (calculated for $C_{18}H_{16}Br_4N_4NaO_4^+$: 690.77973)
IR (KBr, ν [cm$^{-1}$]): 1678, 1697 (Lactam)

Example 9

1-Allyl-5-bromoethynyluracil (I)

C9H7BrN2O2 Mw 255.07
0.61 mL (2.5 mmol) BSA and a few drops of chlorotrimethylsilane are added to a suspension of 215 mg (1 mmol) 5-bromoethynyluracil (1) in 40 mL absolute dichloroethane and stirred at room temperature until a clear solution forms. After adding 0.10 mL (1.2 mmol) allyl bromide and a catalytic quantity of iodine, the mixture is heated for 24 h at reflux under a protective gas atmosphere. The batch is absorbed on silica gel and purified by column chromatography (solvent III).

Yield: 110 mg (43% of theory)
Melting point: 164-168° C.
$^1$H-NMR (δ [ppm]): 4.27 (d, 2H, H-1'); 5.12-5.19 (m, 2H, H-3'); 5.82-5.91 (m, 1, H-2'); 8.09 (s, 1H, H-6); 11.63 (s, 1H, —NH)
$^{13}$C-NMR (δ [ppm]): 50.4 (C-1'); 55.3 (═C—Br); 73.2 (—C═); 98.0 (C-5); 118.6 (C-3'); 133.3 (C-2'); 150.3 (C-6); 150.5 (C-2); 162.8 (C-4)
MS (ESI positive, acetone) m/z: 276.95841 [M+Na]$^+$ (calculated for C9H7BrN2NaO2$^+$: 276.95831) 530.92785 [2M+Na]$^+$ (calculated for C18H14Br2N4NaO4$^+$: 530.92740)
IR (KBr, ν [cm$^{-1}$]): 1628, 1708 (Lactam); 2200 (Ethynyl)

Example 10

5-(2,2-Dibromovinyl)-2'-deoxyuridine (α and β anomers, K and J)

590 mg (2 mmol) 5-(2,2-dibromovinyl)uracil (3), 1.2 mL BSA, and a few drops of chlorotrimethylsilane are suspended in 50 mL absolute dichloroethane and stirred at room temperature until a clear solution has formed. Then 775 mg (1.8 mmol) 2-deoxy-3,5-di-O-(p-chlorobenzoyl)-D-ribofuranosyl chloride (4) dissolved in 20 mL absolute dichloroethane are added to the batch along with catalytic quantities of tin (IV) chloride. The reaction takes place at room temperature under an argon atmosphere over a period of 12 h. After the end of the reaction the solvent is removed in the vacuum, and the residue is purified by column chromatography (solvent III). The α and β anomers of 5-(2,2-dibromovinyl)-1-[2'-deoxy-3',5'-di-O-(p-chlorobenzoyl)]uridine are obtained in a total yield of 1.03 g (74% of theory). The first eluted substance is the β anomer (590 mg, 42% of theory).

To remove the protecting group, 170 mg (0.25 mmol) β anomer of 5-(2,2-dibromovinyl)-1-[2'-deoxy-3',5'-di-O-(p-chlorobenzoyl)]uridine are suspended in 10 mL 0.1 M sodium methylate solution and cooled to 0° C. The course of the reaction is followed by DC (solvent I, and after about two hours of stirring, a high acid ion exchanger for water-free medium is added to neutralize the solution. The separated ion exchanger is washed several times with methanol, and the combined solutions are concentrated. After taking up the oily residue in ether, a white precipitate forms. It is filtered out and rinsed with ether. K is prepared in an analogous way starting with the α anomer of 5-(2,2-dibromovinyl)-1-[2'-deoxy-3',5'-di-O-(p-chlorobenzoyl)]uridine.

α anomer (K)

$C_{11}H_{12}Br_2N_2O_5$ Mw 412.04

Yield: 80 mg (78% of theory)

Melting point: 175-179° C.

$^1$H-NMR (δ [ppm]): 1.91 (d, 1H, H-2'); 2.50-2.59 (m, 1H, H-2'); 3.35-3.38 (m, 2H, H-5'); 4.18-4.21 (2H, H-4', H-3'); 4.83 (1H, —OH); 5.21 (1H, —OH); 6.08 (d, 1H, H-1'); 7.25 (s, 1H, —CH=CBr2); 8.56 (s, 1H, H-6); 11.57 (s, 1H, —NH)

$^{13}$C-NMR (Pyridine-d5, δ [ppm]): 40.9 (C-2'); 62.4 (C-5'); 71.2 (C-3'); 87.5 (C-1'); 88.3 (—CH=CBr2); 90.9 (C-4'); 108.7 (C-5); 128.9 (—CH=CBr2); 140.6 (C-6); 150.0 (C-2); 162.4 (C-4)

MS (ESI positive, Methanol) m/z: 434.9 [M+Na]$^+$ (KBr, ν [cm$^{-1}$]): 1689 (Lactam)

β Anomer (J):

$C_{11}H_{12}Br_2N_2O_5$ Mw 412.04

Yield: 70 mg (68% of theory)

Melting point: 185-190° C.

$^1$H-NMR (δ [ppm]): 2.07-2.15 (m, 2H, H-2'); 3.53-3.56 (m, 2H, H-5'); 3.81 (dd, 1H, H-4'); 4.21 (1H, H-3'); 4.96 (1H, —OH); 5.24 (1H, —OH); 6.17 (t, 1H, H-1'); 7.22 (s, 1H, —CH=CBr2); 8.40 (s, 1H, H-6); 11.64 (s, 1H, —NH)

$^{13}$C-NMR (Pyridine-d5, δ [ppm]): 40.8 (C-2'); 62.1 (C-5'); 71.4 (C-3'); 85.5 (C-1'); 88.4 (—CH=CBr2); 89.7 (C-4'); 109.9 (C-5); 129.1 (—CH=CBr2); 139.8 (C-6); 150.1 (C-2); 162.1 (C-4)

MS (EI positive) m/z: 411.9 [M]+; 295.9 [M-C5H9O3]+

IR (KBr, ν [cm$^{-1}$]): 1676, 1714 (Lactam)

Example 11

1-Benzyl-5-(2,2-dibromovinyl)uracil (L)

$C_{13}H_{10}Br_2N_2O_2$ Mw 386.04

The reaction takes place by analogy with the general preparation method for benzyl-substituted uracil derivatives, from (3) and benzyl bromide.

Yield: 310 mg (80% of theory)

Melting point: 205-206° C.

$^1$H-NMR (δ [ppm]): 4.94 (s, 2H, N—CH2-); 7.21 (s, 1H, —CH=CBr2); 7.28-7.36 (m, 5H, Aromatic); 8.28 (s, 1H, H-6); 11.69 (s, 1H, —NH)

$^{13}$C-NMR (δ [ppm]): 51.6 (N—CH$_2$—); 89.9 (—CH=CBr2); 109.6 (C-5); 128.3 (C-2' and C-6'); 128.5 (C-4'); 129.1 (—CH=CBr2); 129.4 (C-3' and C-5'); 137.1 (C-1'); 144.8 (C-6); 150.6 (C-2); 162.5 (C-4)

MS (ESI positive, methanol) m/z: 406.90024 [M+Na]$^+$ (calculated for $C_{13}H_{10}Br_2N_2NaO_2^+$: 406.90012) 790.81163 [2M+Na]$^+$ (calculated for $C_{26}H_{20}Br_4N_4NaO_4^+$: 790.91103

IR (KBr, ν [cm$^{-1}$]): 1666; 1713 (Lactam)

Example 12

1-(1-Phenylethyl)-5-(2,2-dibromovinyl)uracil (M)

C14H12Br2N2O2 Mw 400.07

The reaction takes place by analogy with the general preparation method for benzyl-substituted uracil derivatives, from (3) and 1-phenylethyl bromide.

Yield: 140 mg (35% of theory)

Melting point: 179-183° C.

$^1$H-NMR (DMSO-d6, δ [ppm]): 1.66 (d, 3H, —CH3); 5.46 (q, 1H, N—CH—); 7.18 (s, 1H, —CH=CBr2); 7.28-7.38 (m, 5H, Aromatic); 8.02 (s, 1H, H-6); 11.70 (s, 1H, —NH)

$^{13}$C-NMR (DMSO-d6, δ [ppm]): 19.3 (—CH3); 54.6 (N—CH—); 89.7 (—CH=CBr2); 109.7 (C-5); 127.7 (C-2' and C-6'); 128.7 (C-4'); 129.0 (—CH=CBr2); 129.5 (C-3' and C-5'); 140.5 (C-1'); 141.4 (C-6); 150.5 (C-2); 162.0 (C-4)

MS (ESI positive, acetone) m/z: 420.91561 [M+Na]$^+$ (calculated for $C_{14}H_{12}Br_2N_2NaO_2^+$: 420.91577) 818.84243 [2M+Na]$^+$ (calculated for $C_{28}H_{24}Br_4N_4NaO_4^+$: 818.84233

IR (KBr, ν [cm$^{-1}$]): 1658; 1699 (Lactam)

Example 13

1-(1-Phenylethyl)-5-bromoethynyluracil (N)

$C_{14}H_{11}Br_2N_2O_2$ Mw 400.07

The reaction takes place by analogy with the general preparation method for benzyl-substituted uracil derivatives, from (1) and 1-phenyl ethyl bromide.

Yield: 100 mg (31% of theory)

Melting point: 163-167° C.

$^1$H-NMR (δ [ppm]): 1.66 (d, 3H, —CH3); 5.71 (q, 1H, N—CH—); 7.29-7.36 (m, 5H, Aromatic); 8.11 (s, 1H, H-6); 11.69 (s, 1H, —NH)

$^{13}$C-NMR (δ [ppm]): 19.0 (—CH3); 54.7 (N—CH—); 55.6 (≡C—Br); 73.4 (—C≡); 98.6 (C-5); 127.4 (C-2' and C-6'); 128.6 (C-4'); 129.4 (C-3' and C-5'); 140.8 (C-1'); 147.3 (C-6); 150.6 (C-2); 162.3 (C-4)

MS (ESI positive, acetone) m/z: 340.98969 [M+Na]$^+$ (calculated for $C_{14}H_{11}BrN_2NaO_2^+$: 340.98961) 658.99051 [2M+Na]$^+$ (calculated for $C_{28}H_{22}Br_2N_4NaO_4^+$: 658.99000

IR (KBr, ν [cm$^{-1}$]): 1686 (Lactam); 2203 (Ethynyl)

Example 14

1-(3,4-Difluorobenzyl)-5-(2,2-dibromovinyl)uracil (O)

$C_{13}H_8Br_2F_2N_2O_5$ Mw 422.03

The reaction takes place by analogy with the general preparation method for benzyl-substituted uracil derivatives, from (3) and 3,4-difluorobenzyl bromide.

Yield: 170 mg (40% of theory)

Melting point: 154-155° C.

$^1$H-NMR (δ [ppm]): 4.92 (s, 2H, N—CH2-); 7.20 (s, 1H, —CH=CBr2); 7.20-7.43 (m, 3H, Aromatic); 8.28 (s, 1H, H-6); 11.71 (s, 1H, —NH)

$^{13}$C-NMR (δ [ppm]): 50.0 (N—CH2-); 89.5 (—CH=CBr2); 109.2 (C-5); 117.0-117.9 (dd, C-2' and C-5', $^2$JC-F=17 Hz); 128.5 (—CH=CBr2); 124.7-124.8 (m, C-6', $^3$JC-F=7 Hz, $^4$JC-F=3 Hz); 134.2 (m, C-1', $^3$JC-F=6 Hz, $^4$JC-F=4 Hz); 144.0 (C-6); 149.0 (dd, C-4', $^1$JC-F=246 Hz, $^2$JC-F=21 Hz); 149.2 (dd, C-3', $^1$JC-F=243 Hz, $^2$JC-F=22 Hz); 149.9 (C-2); 161.8 (C-4)

$^{19}$F-NMR (δ [ppm]): −140.3 to −140.2 (m, 1F, Aromatic); −138.7 to −138.5 (m, 1F, Aromatic)

MS (ESI positive, acetone) m/z: 442.88115 [M+Na]$^+$ (calculated for $C_{13}H_8Br_2F_2N_2NaO_2^+$: 442.88128 862.77420 [2M+Na]$^+$ (calculated for $C_{26}H_{16}Br_4F_4N_4NaO_4^+$: 862.77334

IR (KBr, ν [cm$^{-1}$]): 1670; 1696 (Lactam)

Example 15

1-Benzyl-5-(trimethylsilylethynyl)uracil (P)

$C_{16}H_{18}N_2O_2Si$ Mw 298.42

The reaction takes place by analogy with the general preparation method for benzyl-substituted uracil derivatives, from (6) and benzyl bromide.

Yield: 160 mg (54% of theory)
Melting point: 213-215° C.

$^1$H-NMR (δ [ppm]): 0.16 (s, 9H, —CH3); 4.87 (s, 2H, N—CH2-); 7.28-7.34 (m, 5H, Aromatic); 8.27 (s, 1H, H-6); 11.66 (s, 1H, —NH)

$^{13}$C-NMR (δ [ppm]): 0.6 (—CH3); 51.4 (N—CH2-); 97.8 (—C≡); 98.4 (≡C—Si); 98.5 (C-5); 128.3 (C-2' and C-6'); 128.5 (C-4'); 129.3 (C-3' and C-5'); 137.1 (C-1'); 150.5 (C-6); 150.7 (C-2); 162.6 (C-4)

MS (ESI positive, acetone) m/z: 321.10307 [M+Na]$^+$ (calculated for $C_{16}H_{18}N_2NaO_2Si^+$: 321.10298) 619.21687 [2M+Na]$^+$ (calculated for $C_{32}H_{36}N_4NaO_4Si_2^+$: 619.21673

IR (KBr, ν [cm$^{-1}$]): 1682, 1712 (Lactam); 2167 (Ethynyl)

Example 16

1-(3,4,5-Trimethoxybenzyl)-5-(2,2-dibromovinyl) uracil (Q)

$C_{16}H_{16}Br_2N_2O_5$ Mw 476.0

The reaction takes place by analogy with the general preparation method for benzyl-substituted uracil derivatives, from (3) and 3,4,5-trimethoxybenzyl chloride.

Yield: 210 mg (44% of theory)
Melting point: 171-174° C.

$^1$H-NMR (δ [ppm]): 3.61 (s, 3H, —OCH3); 3.73 (s, 6H, —OCH3); 4.84 (s, 2H, N—CH2-); 6.66 (s, 2H, H-2' and H-6'); 7.20 (s, 1H, —CH=CBr2); 8.25 (s, 1H, H-6); 11.68 (s, 1H, —NH)

$^{13}$C-NMR (δ [ppm]):
51.6 (N—CH2-); 56.6 (2C; —OCH3); 60.7 (—OCH3); 89.7 (—CH=CBr2); 106.1 (C-2' and C-6'); 109.5 (C-5); 129.3 (—CH=CBr2); 132.6 (C-1'); 137.8 (C-4'); 144.6 (C-6); 150.7 (C-2); 153.7 (C-3' and C-5'); 162.5 (C-4)

MS (ESI positive, methanol) m/z: 496.93143 [M+Na]$^+$ (calculated for $C_{16}H_{16}Br_2N_2NaO_5^+$: 496.93182)

IR (KBr, ν [cm$^{-1}$]): 1670, 1703 (Lactam)

Example 17

1-Benzyl-5-ethynyluracil (R)

$C_{13}H_{10}N_2O_2$ Mw 226.24

The reaction takes place by analogy with the general preparation method for benzyl-substituted uracil derivatives, from (5) and benzyl bromide.

Yield: 140 mg (62% of theory)
Melting point: 190-193° C.

$^1$H-NMR (δ [ppm]): 4.10 (s, 1H, ≡CH); 4.87 (s, 2H, N—CH2-); 7.28-7.35 (m, 5H, Aromatic); 8.26 (s, 1H, H-6); 11.66 (s, 1H, —NH)

$^{13}$C-NMR (δ [ppm]): 51.5 (N—CH2-); 76.8 (—C≡); 84.5 (≡CH); 97.9 (C-5); 128.2 (C-2' and C-6'); 128.5 (C-4'); 129.4 (C-3' and C-5'); 137.1 (C-1') 150.3 (C-6); 150.7 (C-2); 162.8 (C-4)

MS (ESI positive, methanol) m/z: 249.06366 [M+Na]$^+$ (calculated for C13H10N2NaO2$^+$: 246.06345) 475.13783 [2M+Na]$^+$ (calculated for C26H20N4NaO4$^+$: 475.13768)

IR (KBr, ν [cm$^{-1}$]): 1679, 1705 (lactam); 2111 (ethynyl)

Example 18

Octadec-9-enoic acid [5-(1,3-dioxo-1,3-2H-dihydroisoindol-2-yl)-2,6-dioxopiperidin-3-yl]amide (T)

JNT 136B
$C_{31}H_{43}N_3O_5$ Mw 537.7

0.31 g (1.0 mol) 5'-aminothalidomide HCl and 0.31 g (1.1 mmol) oleic acid are suspended in 8 mL dry dichloromethane, and the flask is closed with a septum. After adding 170 μL triethylamine, the suspension is cooled to 15° C. in a NaCl ice bath. A solution of 10 mg DMAP and 0.21 g (1.0 mmol) DCC in 4 mL dry chloromethane are added to the batch dropwise via a syringe. After heating to room temperature the batch is stirred overnight. The batch is cooled in an ice bath, the precipitate is suctioned out and discarded (dicyclohexylurea). 10 mL dichloromethane is added to the filtrate, and the solution is extracted once with a mixture of 10 mL water and two drops of concentrated hydrochloric acid and once with water. The organic phase is dried over sodium sulfate and the sulfate is completely removed on a rotary evaporator. The resulting product still contains small amounts of dicyclohexylurea. Further purification can take place by brief heating to reflux in dichloromethane/petroleum ether and hot filtering of the precipitate through a frit.

Yield: 160 mg (29.8% of theory)
Melting range: 193-201° C.

$^1$H-NMR (DMSO-d$_6$, δ [ppm]): 0.80-0.85 (m, 3H, CH3); 1.12-1.34 (m, 20H, [—CH$_2$—]$_n$); 1.41-1.48 (m, 2H, —CO—CH2-CH$_2$—); 1.90-1.98 (m, 4H, CH$_2$—CH=CH—CH$_2$); 2.04-2.13 (m, 3H, C4'-H+—NH—CO—CH$_2$—); 2.64-2.79 (m, 1H, C4'-H); 4.90-5.01 (m, 1H, C3'-H); 5.26-5.30 (m, 2H, —CH=CH—); 5.40 (dd, 1H, C5'-H), $^3$J$_{H,H}$=13.2; 5.4 Hz); 7.87-7.96 (m, 4H, ArH); 8.23 (d, 1H, Amide-NH, $^3$J$_{H,H}$=8.1 Hz); 11.28 (s, 1H, Imide-NH)

$^{13}$C-NMR (DMSO-d6, δ [ppm]): 14.6 (—CH$_3$); 22.8; 25.8; 27.2; 27.3; 29.2-29.8 (m); 32.0; 35.9 ([—CH$_2$—]$_n$+C4'); 49.1, 49.2 (C3'+C5'); 124.0; 124.3 (C4, C7); 130.3 (C=C); 131.9 (C3a, C7a); 135.6 (C5, C6); 167.6; 167.8; 170.2; 172.5; 172.8 (CO)

MS (ESI positive, CH$_2$Cl$_2$/MeOH/Na$^+$) m/z: 560.30992 [M+Na]$^+$ (calculated for $C_{31}H_{43}N_3NaO_5^+$: 560.30949); 1097.63107 [2M+Na]$^+$ (calculated for $C_{62}H_{86}N_6NaO_{10}^+$: 1097.62976

IR (KBr, ν [cm$^{-1}$]): 2925, 2853, 1725, 1396, 719

Example 19

1-(2-Adamantan-1-yl-ethyl)-5-trimethylsilanylethynyluracil (U)

$C_{21}H_{30}N_2O_2Si$ Mw=370.6

416 mg (2 mmol) dried 5-TMSU (5-trimethylsilanylethynyluracil) are suspended in about 50 mL absolute MeCN, 1.2 mL (5 mmol) BSA, and a few drops of chlorotrimethylsilane are added through a septum, and the mixture is stirred at room temperature under argon until the suspension is completely clear. Then 585 mg (2.4 mmol) 1-(2-bromoethyl)adamantane and a little $I_2$ are added to the resulting solution. The batch is kept under exclusion from moisture for 4 days in an oil bath at reflux and for another 3 days at room temperature. The course of the reaction is followed by thin layer chromatography (ethyl acetate/hexane 1:2).

The solvent is removed in a vacuum, the residue is taken up with $CHCl_3/H_2O$ and washed with $H_2O$, and the organic phase is separated and dried over $Na_2SO_4$. The solvent is again removed and the oily residue is taken up with a little $CHCl_3$ and chromatographically separated. The resulting fractions are concentrated, the oily residue with mixed with MeOH and the resulting crystals are separated.

Column chromatography: Column 350 mm, 30 mm OD, (flash gel, 70 g), solvent: 100% $CHCl_3$ Yield: 55 mg (7.4% of theory)

$^1$H-NMR ($CDCl_3$, δ [ppm]): 0.23 (s, 9H, $S_1$—$CH_3$); 1.45-1.47 (m, 2H, —$CH_2$—$CH_2$—); 1.54 (d, 6H, —C—$CH_2$-Ad-); 1.61-1.71 (m, 6H, 13 CH—$CH_{2-Ad}$—); 1.98 (m, 3H, —$CH_2$—$CH_{Ad}$—); 3.72-3.77 (m, 2H, N—$CH_2$—); 7.44 (s, 1H, H-6); 8.60 (s, br, 1H, —NH)

$^{13}$C-NMR ($CDCl_3$, δ [ppm]): 0.01 (Si—$CH_3$); 28.58 ($CH_{Ad}$); 32.09 ($C_{Ad}$); 37.02 ($CH_{2-Ad}$); 42.29 (C—$CH_{2-Ad}$); 43.34 (—$CH_2$—$CH_{2-Ad}$); 44.79 (N—$CH_2$—$CH_{2-Ad}$); 95.19 (—C≡); 99.87 (≡C—Si); 100.23 (C-5); 147.72 (C-6); 149.58 (C-2); 161.59 (C-4)

MS (ESI positive, $CHCl_3$/methanol/sodium formate) m/z: [M+H]$^+$371.21493 (calculated for $C_{21}H_{31}N_2O_2Si^+$: 371.21547) [2M+H]$^+$741.42259 (calculated for $C_{42}H_{61}N_4O_4Si_2^+$: 741.42311)

Example 20

1-Benzyl-5-(4-trimethylsilanyl-2-trimethylsilanylethynylbut-1-en-3-inyl)uracil (V)

$C_{23}H_{28}N_2O_2Si_2$ Mw=420.7

To a mixture of 185 mg (0.48 mmol) 1-benzyl-5-(2,2-dibromovinyl)uracil, 10 mg (0.053 mmol) CuI, 28 mg (0.024 mmol) [$(C_6H_5)_3P]_2PdCl_2$, and 110 μL, (0.76 mmol) TMSA in 25 mL absolute ethyl ether under argon is added, after 10 min, 176 μL (0.96 mmol) N-ethyl diisopropylamine at room temperature. The yellow suspension becomes clear after 10 min and slowly turns dark. It is stirred for 24 h at RT (DC control); the batch is quenched with 2 mL water, taken up in 100 mL ethyl ether, and washed with water. The organic phase is dried over $Na_2SO_4$, the solvent is removed in a vacuum, the raw product is taken up with a little $CHCl_3$, and then chromatographically purified.

Column chromatography: Column 400 mm, 30 mm AD (70 g flash gel, 5% deactivated)

Solvent: 100% $CHCl_3$ or $CHCl_3$/MeOH/450:1.71 as gradient

DC control: ethyl acetate/hexane 2:1

Yield: 23 mg (11.4% of theory)

MS (ESI positive, $CHCl_3$/methanol/sodium formate) m/z: [M+H]$^+$443.15815 (calculated for $C_{23}H_{28}N_2NaO_2Si_2^+$: 443.15869) [2M+H]$^+$863.32708 (calculated for $C_{46}H_{56}N_4NaO_4Si_4^+$: 863.32762)

Example 21

3-(2-Adamantan-1-ylethyl)-1-benzhydryl-5-ethynyluracil (W)

$C_{31}H_{32}N_2O_2$ Mw=464.6

115 mg (0.38 mmol) 1-benzhydril-5-ethynyluracil and 120 mg (0.41 mmol) 1-(2-iodoethyl)adamantane are dissolved in 25 mL DMF. 400 mg $K_2CO_3$ are added to the clear solution and stirred for 24 h at room temperature. The solvent is removed in a vacuum at 60° C. and the yellow residue is taken up in an $H_2O/CH_2Cl_2$ (1:1) mixture. The mixture is extracted two more times, each time with 30 mL $CH_2Cl_2$, and the organic phase is dried over $Na_2SO_4$. The solvent is again removed, and the oily residue is taken up with a little $CHCl_3$ and chromatographically separated. The fractions are concentrated, the oily residue is mixed with MeOH, and the resulting crystals are separated.

Front chromatography, column (200 mm) with frit, 2.4 cm [OV] (flash gel 45 g)

Solvent: $CHCl_3$ 150 mL

DC control: ethyl acetate:hexane/1:2

Yield: 116 mg (65.7% of theory)

Melting point: 183-186° C. (from MeOH)

$^1$-NMR ($CDCl_3$, δ [ppm]): 1.36-1.41 (m, 2H, —$CH_2$—$CH_2$—); 1.57 (d, 6H, —C—$CH_{2-Ad}$—); 1.66 (m, 6H, —CH—$CH_{2-Ad}$—); 1.94 (m, 3H, —$CH_2$—$CH_{Ad}$—); 3.10 (s, 1H, (≡CH); 3.97-4.03 (m, 2H, N—$CH_2$—); 7.08 (s, 1H, N—CH—); 7.13-7.16 (m, 5H, Aromatic); 7.32 (s, 1H, H-6); 7.37-7.44 (m, 5H, Aromatic)

$^{13}$C-NMR ($CDCl_3$, δ [ppm]): 28.73 ($CH_{Ad}$); 32.21 ($C_{Ad}$); 37.22 ($CH_{2-Ad}$); 38.03 (N—$CH_2$—$CH_{2-Ad}$—); 41.00 (—$CH_2$—$CH_{2-Ad}$); 42.00 (C—$CH_2$-Ad); 63.88 (N—CH—); 75.54 (≡CH); 81.56 (—C≡); 98.14 (C-5); 128.59, 128.86, 129.38 (8C, Aromatic); 137.32 (2C, $C_q$-Aromatic); 143.87 (C-6); 150.76 (C-2); 161.13 (C-4)

MS (ESI positive, acetone/methanol/sodium formate) m/z: [M+Na]$^+$487.23560 (calculated: 487.23614) [2M+Na]$^+$951.48198 (calculated: 951.48250)

Example 22

1-Benzhydryl-5-trimethylsilanylethynyluracil (X)

$C_{22}H_{22}N_2O_2Si$ Mw=374.52

2.09 g (10 mmol) 5-TMSU (5-trimethylsilanylethynyluracil) dried over $P_4O_{10}$ are suspended in about 50 mL absolute MeCN, then 6 mL (25 mmol) BSA and a few drops of chlorotrimethylsilane are added via a septum, and the suspension is stirred at room temperature under argon until it is completely clear. Then 2.72 g (11 mmol) 1-bromodiphenylmethane are added to the resulting solution. The batch is now stirred for 24 h on an oil bath under exclusion from moisture at 84° C. The dark brown solution is concentrated and left to stand in the ice bath. The brown raw product that precipitates is separated, washed with a little cold MeCN, and recrystallized from about 50 mL MeCN.

Yield: 1.51 g (40.3% of theory)

Example 23

3-Benzyl-(E)-5-(2-bromovinyl)-2'-deoxyurindine, β-anomer (Y)

$C_{18}H_{19}BrN_2O_5$ Mw 423.3

666 mg (2 mmol) BVDU and 410 mg (2.4 mmol) benzyl bromide are dissolved in 25 mL DMF. 1 g $K_2CO_3$ is added to the clear solution and stirred for 20 h at RT. The solvent is removed at 50° C., and the solid residue is dissolved in an $H_2O/CH_2Cl_2$ mixture. The mixture is extracted two times with water/NaCl (saturated), and the organic phase is dried over $Na_2SO_4$. Purification takes place via a connected column chromatography:

Short column (200 mm) with frit, 2.4 cm OD (flash gel, 25 g)

Solvent: 100% $CHCl_3$, 110 mL, then $CHCl_3$:MeOH/30:1

DC control: ethyl acetate:hexane/2:1

Yield: 631 mg (74% of theory)

$^1$H-NMR (DMSO-$d_6$, δ [ppm]): 2.16-2.19 (m, 2H, H-2'); 3.58-3.63 (m, 2H, H-5'); 3.79 (m, 1H, H-4'); 4.24 (m, 1H, H-3'); 4.96-5.02 (m, 2H, N—$CH_2$—); 5.10 (t, 1H, —OH-5'); 5.25 (d, 1H, —OH-3'), 6.16 (t, 1H, H-1'); 6.88 (d, 1H, —CH=, $^3J_{H-H}$=13.5 Hz); 7.23-7.28 (m, 2H, Aromatic); 7.25 (d, 1H, =CHBr, $^3J_{H-H}$=13.5 Hz), 8.15 (s, 1H, H-6)

$^{13}$C-NMR (DMSO-$d_6$, δ [ppm]): 40.00 (C-2'); 43.80 (N—$CH_2$—); 60.80 (C-5'); 69.67 (C-3'); 85.71 (C-1'); 87.68 (C-4'); 108.99 (C-5); 106.81 (=CHBr); 127.22, 127.64 and 128.34 (5C, Aromatic); 129.92 (—CH=); 136.77 ($C_q$, Aromatic); 138.30 (C-6); 149.46 (C-2); 160.55 (C-4)

The invention claimed is:

1. Uracil derivatives of General Formula I:

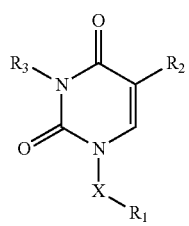

where $R_1$ is chosen from the group consisting of linear or branched $C_2$-$C_{18}$ alkenyl, linear or branched $C_2$-$C_{18}$ alkynyl, unsubstituted or substituted aromatic residues having 6-22 carbon atoms and/or unsubstituted or substituted heteroaromatic residues having 5-22 carbon atoms, $C_5$-$C_8$ cycloalkyl, $C_5$-$C_8$ cycloalkenyl, adamantyl, and the formulas III-IV,

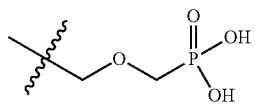

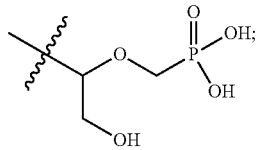

X is a single bond or is chosen from the group consisting of $(CHR_4)_n$ with n=1-3, CO, $CNR_4$, CNOH, SO, and $SO_2$, where $R_4$ is chosen from the group consisting of H, linear or branched $C_1$-$C_{18}$ alkyl, and residues as defined for $R_1$;

$R_2$ is chosen from
  a) unsaturated residues of general formula VI:

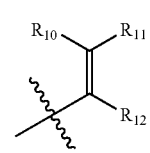

where $R_{10}$ and $R_{11}$ are independently chosen from the group consisting of H, F, Cl, I, CN, $NO_2$, $COOR_{13}$, and $CON(R_{13})_2$, and $R_{12}$ is chosen from the group consisting of H, F, Br, Cl, I, CN, $NO_2$, $COOR_{13}$, and $CON(R_{13})_2$, where $R_{13}$ is H or linear or branched $C_1$-$C_{18}$ alkyl and the residue $R_{10}$ or $R_{11}$ can be arranged in (E) or (Z) conformation;

b) unsaturated residues of general formula (VII),

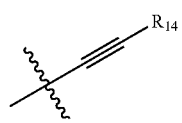

where $R_{14}$ is chosen from the group consisting of H, halogens, $Si(CH_3)_3$, primary, secondary, or tertiary amine or primary, secondary, or tertiary aminomethyl; or c) a residue chosen from the group of compounds of general formulas VIII-X

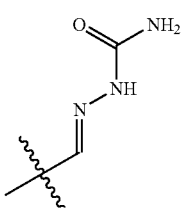

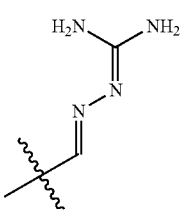

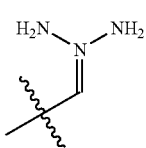

d) CHO, COOR$_{13}$, CH$_2$OR$_{13}$, CON(R$_{13}$)$_2$, or 1,2,3-triazol-4-yl; and R$_3$ is H.

2. The uracil derivative of claim 1, wherein R$_2$ is chosen from:

a) (E)-2-chlorovinyl, (E)-2-iodovinyl, (E)-2-cyanovinyl, 2,2-dicyanovinyl, (E)-2-nitrovinyl, 2,2-dinitrovinyl, (E)-2-carboxyvinyl, (E)-2-cyano-2-carboxyvinyl, vinyl (E)-2-carboxy-C$_1$-C$_8$ alkyl ester, vinyl (E)-2-cyano-2-carboxy-C$_1$-C$_8$ alkyl ester, vinyl (E)-2-carboxylic acid amide, vinyl (E)-2-cyano-2-carboxylic acid amide, vinyl (E)-2-carboxylic acid C$_1$-C$_8$ alkylamide, vinyl (E)-2-cyano-2-carboxylic acid C$_1$-C$_8$ alkylamide, and (Z) isomers thereof; and b) ethynyl, bromoethynyl, and trimethylsilylethynyl.

3. The uracil derivative of claim 1, wherein R$_{14}$ is independently chosen from piperidino, piperazino, morpholino, piperidinomethyl, piperazinomethyl, and morpholinomethyl.

4. The uracil derivative of claim 1, wherein the uracil derivative corresponds to a compound of one of the following formulas:

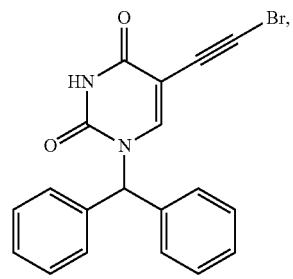

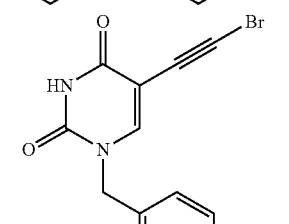

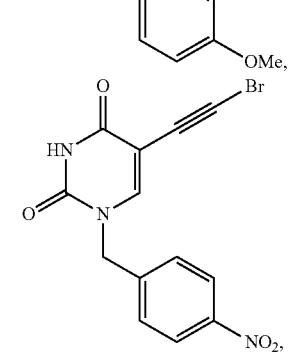

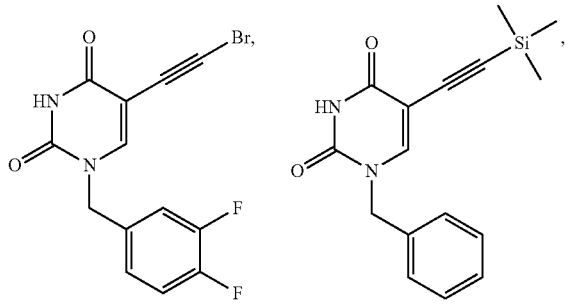

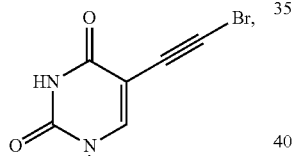

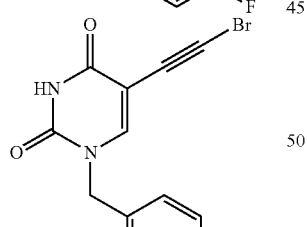

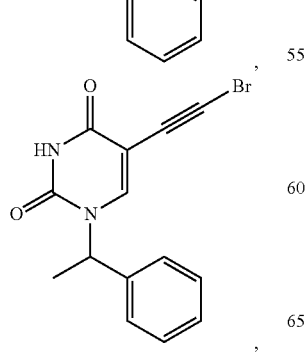

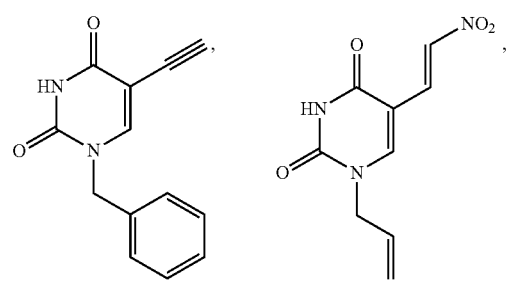

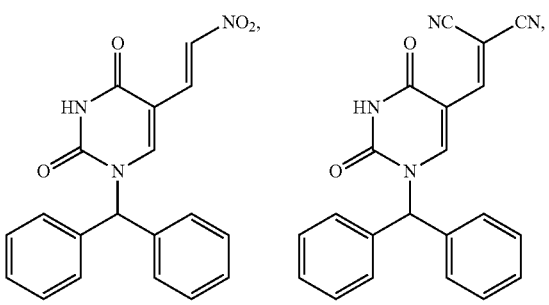

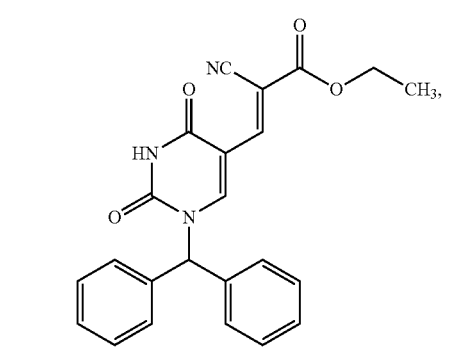

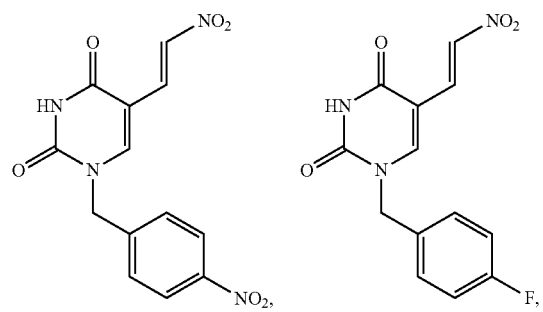

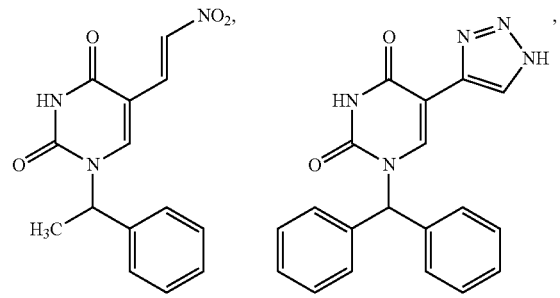
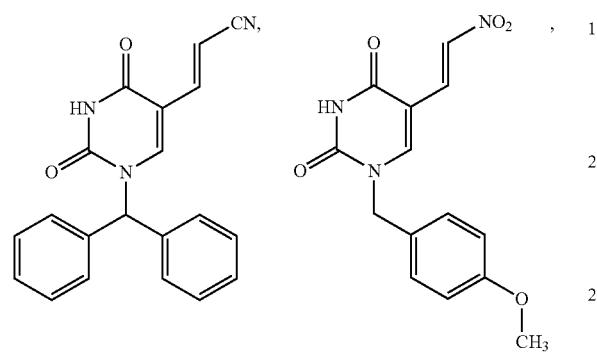
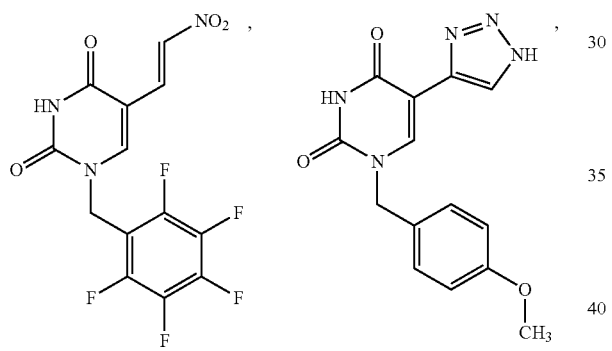
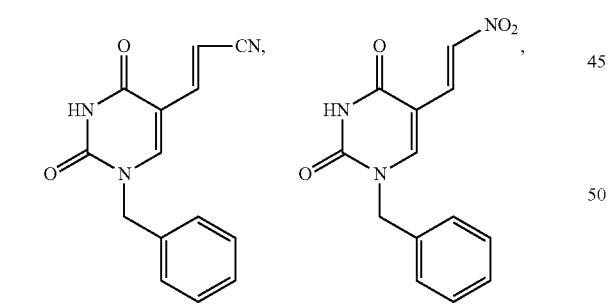
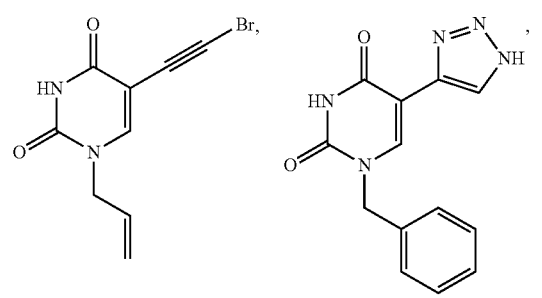
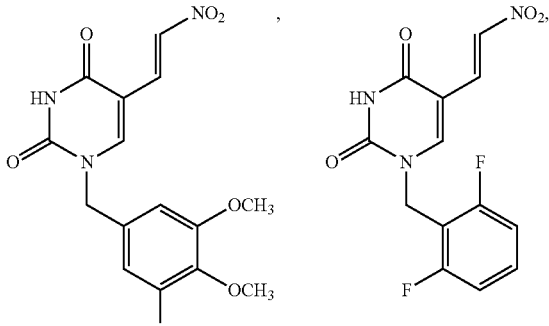
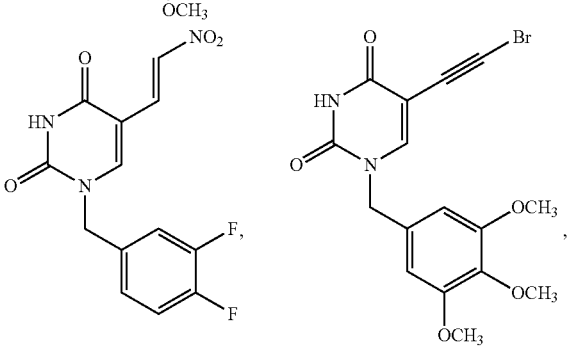
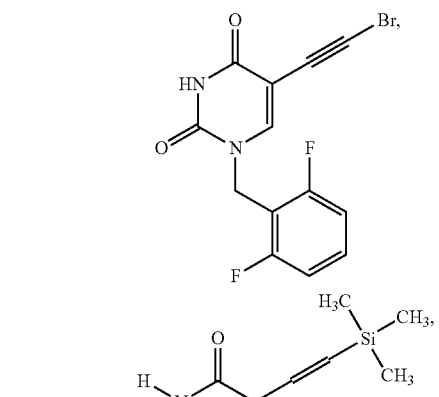
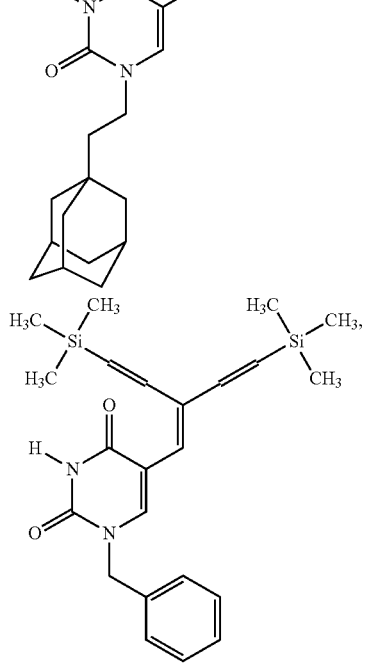

-continued

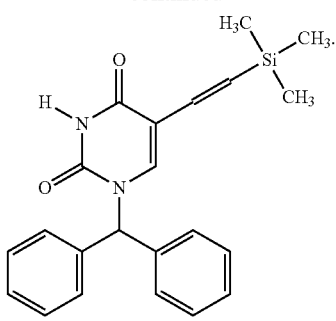

5. A pharmaceutical composition comprising a uracil compound of claim 1 and a pharmaceutically acceptable carrier.

6. Uracil derivatives of General Formula I:

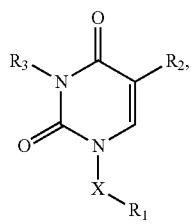

I where $R_1$ is chosen from the group consisting of linear or branched $C_2$-$C_{18}$ alkenyl, linear or branched $C_2$-$C_{18}$ alkynyl, unsubstituted or substituted aromatic residues having 6-22 carbon atoms and/or unsubstituted or substituted heteroaromatic residues having 5-22 carbon atoms, $C_5$-$C_8$ cycloalkyl, $C_5$-$C_8$ cycloalkenyl, adamantyl, and the formulas III-IV,

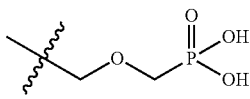

III

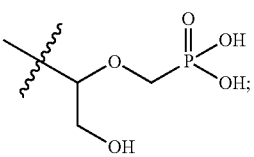

IV

X is a single bond or is chosen from the group consisting of $(CHR_4)_n$ with n=1-3, $CNR_4$, CNOH, SO, and $SO_2$, where $R_4$ is chosen from the group consisting of H, linear or branched $C_1$-$C_{18}$ alkyl, and residues as defined for $R_1$;

$R_2$ is chosen from
a) unsaturated residues of general formula VI:

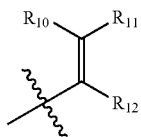

VI where $R_{10}$, $R_{11}$, and $R_{12}$ are independently chosen from the group consisting of H, F, Br, Cl, I, CN, $NO_2$, $COOR_{13}$, and $CON(R_{13})_2$, where $R_{13}$ is H or linear or branched $C_1$-$C_{18}$ alkyl and the residue $R_{10}$ or $R_{11}$ can be arranged in (E) or (Z) conformation;

b) unsaturated residues of general formula (VII),

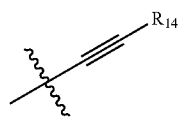

VII where $R_{14}$ is chosen from the group consisting of H, halogens, $Si(CH_3)_3$, primary, secondary, or tertiary amine or primary, secondary, or tertiary aminomethyl; or c) a residue chosen from the group of compounds of general formulas VIII-X

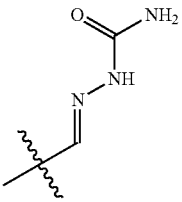

VIII

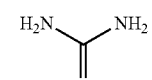

IX

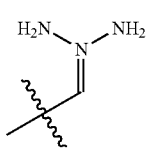

X d) CHO, $COOR_{13}$, $CH_2OR_{13}$, $CON(R_{13})_2$, or 1,2,3-triazol-4-yl; and $R_3$ is H.

7. The uracil derivative of claim 6, wherein $R_2$ is chosen from
a) (E)-2-chlorovinyl, (E)-2-bromovinyl, (E)-2-iodovinyl, (E)-2,2-dibromovinyl, (E)-2-cyanovinyl, 2,2-dicyanovinyl, (E)-2-nitrovinyl, 2,2-dinitrovinyl, (E)-2-carboxyvinyl, (E)-2-cyano-2-carboxyvinyl, vinyl (E)-2-carboxy-$C_1$-$C_8$ alkyl ester, vinyl (E)-2-cyano-2- carboxy-$C_1$-$C_8$ alkyl ester, vinyl (E)-2-carboxylic acid amide, vinyl (E)-2-cyano-2-carboxylic acid amide, vinyl (E)-2-carboxylic acid $C_1$-$C_8$ alkylamide, vinyl (E)-2-cyano-2-carboxylic acid $C_1$-$C_8$ alkylamide, and (Z) isomers thereof; and b) ethynyl, bromoethynyl, and trimethylsilylethynyl.

8. The uracil derivative of claim 6, wherein the uracil derivative corresponds to a compound of one of the following formulas:

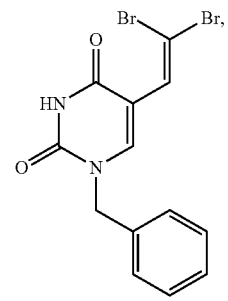
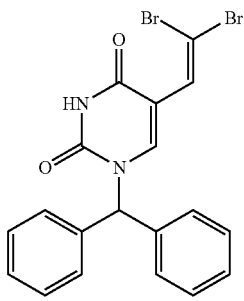
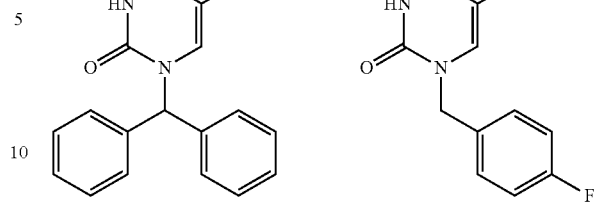
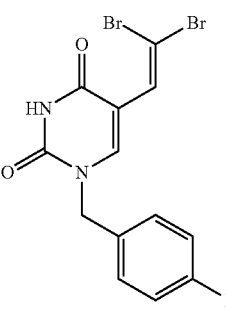
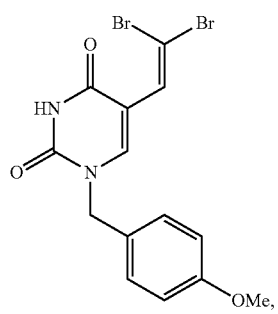
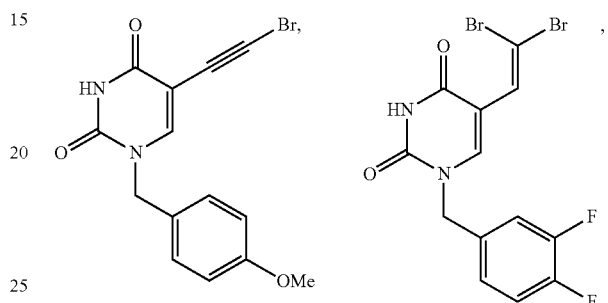
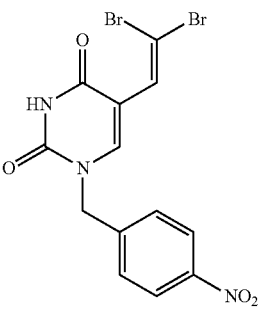
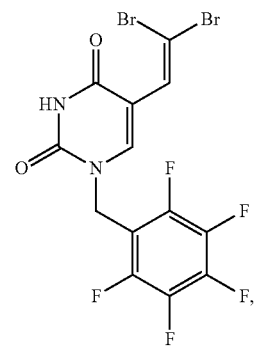
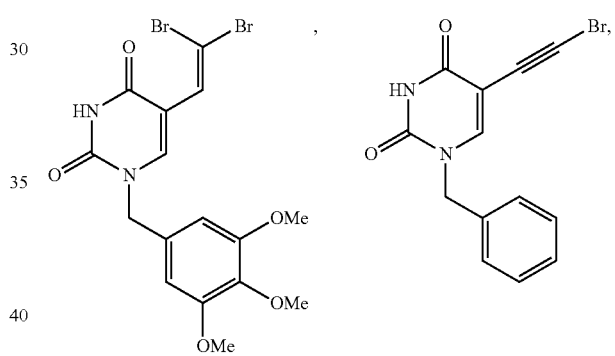
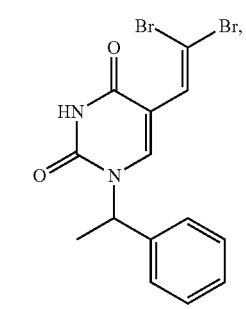
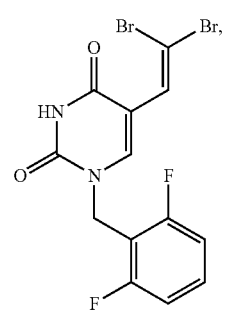
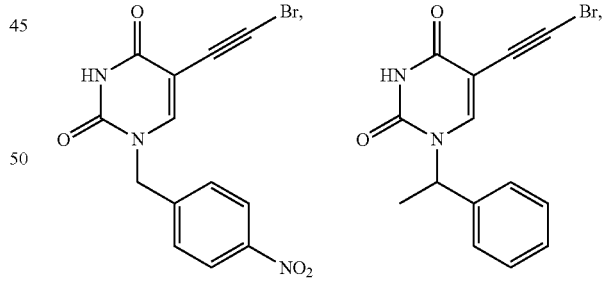
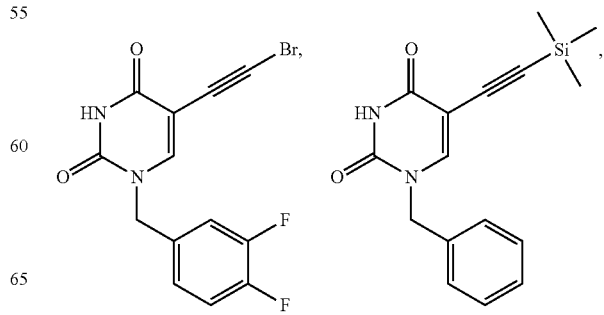

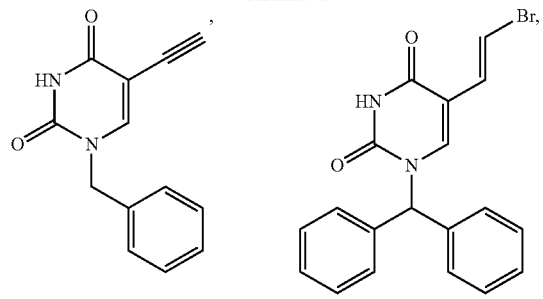
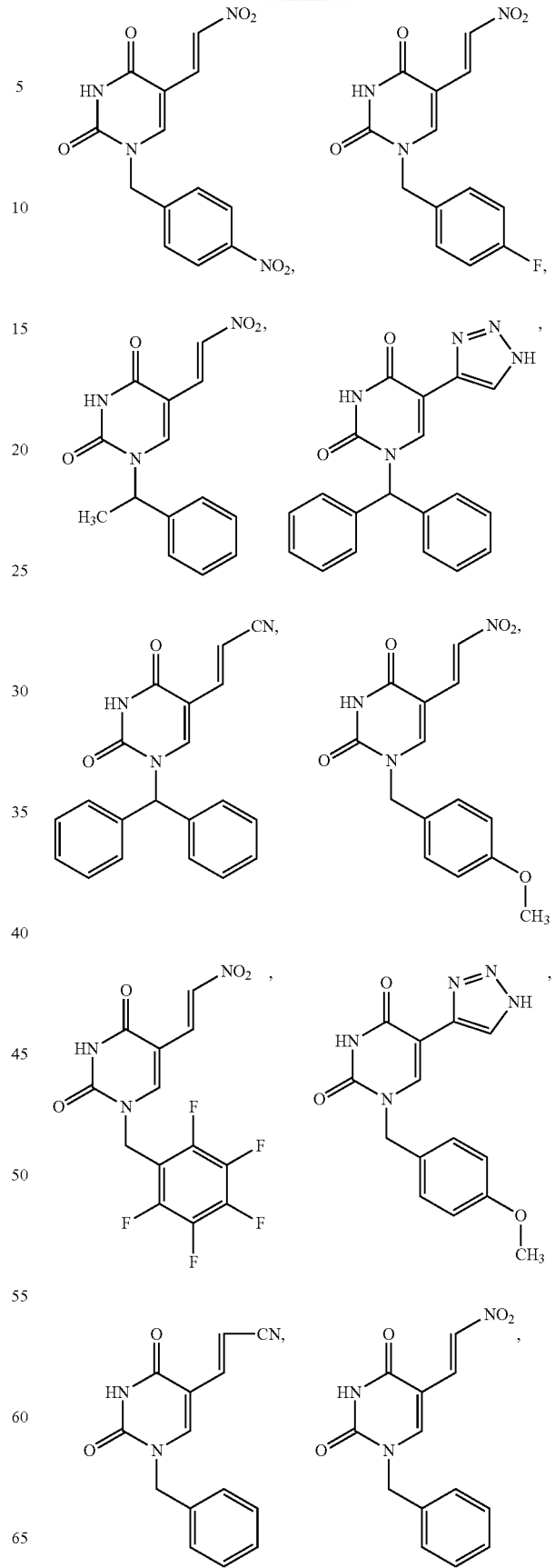

-continued

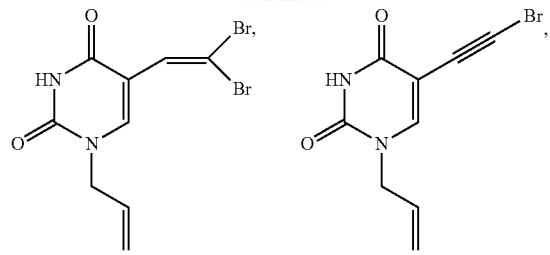

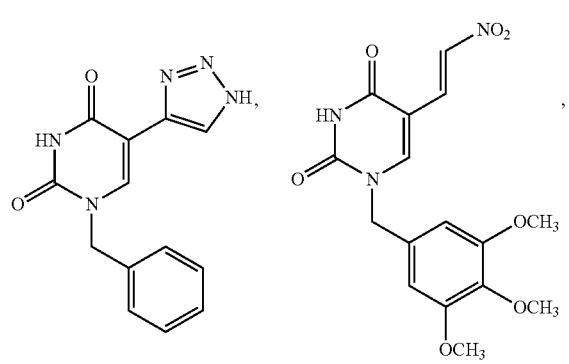

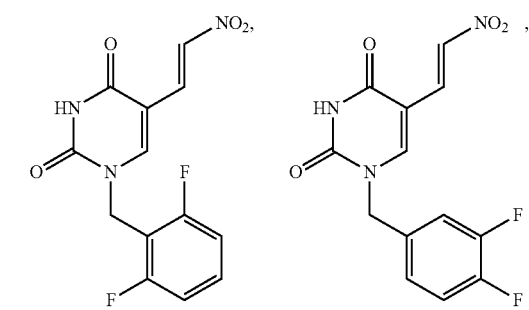

-continued

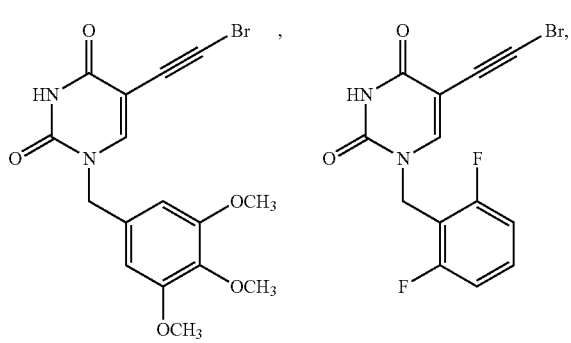

9. A pharmaceutical composition comprising a uracil compound of claim 6 and a pharmaceutically acceptable carrier.

10. A method for suppressing or reducing resistance formation in a patient undergoing cytostatic treatment comprising administering to the patient an effective amount of a uracil compound of claim 1.

11. The method of claim 10, wherein the uracil compound is administered in combination with at least one cytostatic agent.

12. The method of claim 11, wherein the uracil compound is administered as a single formulation in combination with at least one cytostatic agent.

13. The method of claim 11, wherein the uracil compound is administered as a separate formulation from at least one cytostatic agent.

* * * * *